US009567259B2

(12) United States Patent
Amin et al.

(10) Patent No.: US 9,567,259 B2
(45) Date of Patent: Feb. 14, 2017

(54) ANTIMICROBIAL GLASS ARTICLES AND METHODS OF MAKING AND USING SAME

(71) Applicant: CORNING INCORPORATED, Corning, NY (US)

(72) Inventors: Jaymin Amin, Corning, NY (US); Nicholas Francis Borrelli, Elmira, NY (US); Timothy Michael Gross, Waverly, NY (US); Odessa Natalie Petzold, Elmira, NY (US); Wageesha Senaratne, Horseheads, NY (US)

(73) Assignee: Corning Incorporated, Corning, NY (US)

( * ) Notice: Subject to any disclaimer, the term of this patent is extended or adjusted under 35 U.S.C. 154(b) by 8 days.

(21) Appl. No.: 14/176,470

(22) Filed: Feb. 10, 2014

(65) Prior Publication Data
US 2015/0225287 A1    Aug. 13, 2015

(51) Int. Cl.
*B32B 17/00*    (2006.01)
*C03C 21/00*    (2006.01)
*A01N 59/16*    (2006.01)

(52) U.S. Cl.
CPC ............ *C03C 21/005* (2013.01); *A01N 59/16* (2013.01); *C03C 21/002* (2013.01); *Y10T 428/315* (2015.01)

(58) Field of Classification Search
USPC ....... 428/409, 410, 426, 428, 432, 434, 688, 428/689, 697, 699, 701, 702; 65/400, 440, 65/30.13, 30.14
See application file for complete search history.

(56) References Cited

U.S. PATENT DOCUMENTS

| | | | | |
|---|---|---|---|---|
| 3,798,013 | A | * | 3/1974 | Inoue et al. ................. 65/30.14 |
| 5,007,948 | A | | 4/1991 | Araujo .......................... 65/30.13 |
| 6,180,584 | B1 | | 1/2001 | Sawan et al. ................. 510/382 |
| 8,034,732 | B2 | | 10/2011 | Kobayashi et al. ............ 501/71 |
| 8,241,865 | B2 | | 8/2012 | Taintor ........................... 435/29 |

(Continued)

FOREIGN PATENT DOCUMENTS

| | | |
|---|---|---|
| CA | 2734864 A1 | 2/2010 |
| CA | 2476953 C | 6/2012 |

(Continued)

OTHER PUBLICATIONS

Antibacterial Activity and Mechanism of Action of the Silver Ion in Staphylococcus and *Escherichia coli*, Woo Kyung Jung, Hye Cheong Koo, Ki Woo Kim, Sook Shin, So Hyun Kim, Yong Ho Park, Applied and Environmental Microbiology, Apr. 2008, p. 2171-2178, vol. 74, No. 7.

(Continued)

*Primary Examiner* — Lauren R Colgan
(74) *Attorney, Agent, or Firm* — Payal A. Patel; Jie Gao

(57) ABSTRACT

Described herein are various antimicrobial glass articles that have improved resistance to discoloration when exposed to harsh conditions. The improved antimicrobial glass articles described herein generally include a glass substrate that has a low concentration of nonbridging oxygen atoms, a compressive stress layer and an antimicrobial silver-containing region that each extend inward from a surface of the glass substrate to a specific depth, such that the glass article experiences little-to-no discoloration when exposed to harsh conditions. Methods of making and using the glass articles are also described.

27 Claims, 10 Drawing Sheets

(56) References Cited

U.S. PATENT DOCUMENTS

| | | | |
|---|---|---|---|
| 8,586,492 B2 | 11/2013 | Barefoot et al. | |
| 8,753,744 B2 | 6/2014 | Borrelli et al. | |
| 8,969,226 B2 | 3/2015 | Dejneka et al. | |
| 9,156,724 B2 | 10/2015 | Gross | |
| 2005/0020471 A1 | 1/2005 | Cheung et al. | 510/463 |
| 2005/0037058 A1 | 2/2005 | Canada et al. | 424/445 |
| 2005/0044895 A1 | 3/2005 | Yamate et al. | 65/111 |
| 2007/0172661 A1* | 7/2007 | Fechner et al. | 428/409 |
| 2008/0045491 A1 | 2/2008 | Fitchmun | 514/185 |
| 2008/0063728 A1 | 3/2008 | Fechner et al. | 424/618 |
| 2008/0152905 A1 | 6/2008 | Hendriks et al. | 428/365 |
| 2009/0142568 A1 | 6/2009 | Dejneka et al. | 428/220 |
| 2010/0009154 A1* | 1/2010 | Allan et al. | 428/220 |
| 2010/0028607 A1* | 2/2010 | Lee et al. | 428/156 |
| 2010/0071415 A1 | 3/2010 | Voss et al. | 65/22 |
| 2011/0081542 A1* | 4/2011 | Pilloy et al. | 428/341 |
| 2011/0267698 A1* | 11/2011 | Guilfoyle et al. | 359/609 |
| 2012/0034435 A1* | 2/2012 | Borrelli et al. | 428/210 |
| 2012/0048604 A1* | 3/2012 | Cornejo et al. | 174/258 |
| 2012/0135226 A1 | 5/2012 | Bookbinder et al. | |
| 2012/0219792 A1* | 8/2012 | Yamamoto et al. | 428/336 |
| 2013/0130023 A1 | 5/2013 | Boulanger et al. | |
| 2014/0106172 A1 | 4/2014 | Dejneka et al. | |
| 2014/0154292 A1 | 6/2014 | Borrelli et al. | |
| 2014/0356406 A1* | 12/2014 | Patil et al. | 424/411 |
| 2014/0356605 A1 | 12/2014 | Adib et al. | |
| 2014/0370302 A1* | 12/2014 | Amin et al. | 428/426 |
| 2014/0370303 A1* | 12/2014 | Jin et al. | 428/426 |
| 2015/0147775 A1 | 5/2015 | Fiacco et al. | |

FOREIGN PATENT DOCUMENTS

| | | | |
|---|---|---|---|
| CN | 101010004 A | 8/2007 | |
| CN | 101947330 A | 1/2011 | |
| CN | 102293718 A | 12/2011 | |
| CN | 102388002 A | 3/2012 | |
| CN | 102460172 A | 5/2012 | |
| CN | 102477457 A | 5/2012 | |
| EP | 1270527 A1 | 1/2003 | |
| EP | 1814937 B1 | 7/2009 | |
| JP | 10218641 A | 8/1998 | |
| JP | 2000053451 A | 2/2000 | |
| JP | 2003054990 A | 2/2003 | 8/14 |
| JP | 2005022916 A | 1/2005 | 8/8 |
| JP | 2010138025 A | 6/2010 | |
| JP | 2011133800 A | 7/2011 | G06F 9/00 |
| JP | 4816224 b2 | 11/2011 | 59/16 |
| JP | 4916503 B2 | 4/2012 | |
| JP | 2012079133 A | 4/2012 | 3/41 |
| JP | 2012105643 A | 6/2012 | 1/4 |
| KR | 2006029580 A | 4/2006 | 7/2 |
| RU | 2451085 C2 | 5/2012 | 1/2 |
| WO | 2004089431 A1 | 10/2004 | |
| WO | 2007108245 A1 | 9/2007 | |
| WO | 2007137823 A1 | 12/2007 | |
| WO | 2012019067 A1 | 2/2012 | 17/30 |

OTHER PUBLICATIONS

New Strategies in the Development of Antimicrobial Coatings: The Example of Increasing Usage of Silver and Silver Nanoparticles, Menno L. W. Knetsch, Leo H. Koole, Polymers (Journal) 2011, 2, 340-366;doi: 10.3390/polum310340.

Ion-Exchange Equilibria between Glass and Molten Salts, R. J. Araujo et al.,J. Non-Cryst. Sol., 318, 262-267, 2003.

Comparison of the Antibacterial Activity of Chelating Agents Using the Agpar Diffusion Method, A. Hinton Jr. and K. D. Ingram, International Journal of Poultry Science 9(11): 1023-1026, 2010.

Mechanistic study of the antibacterial effect of silver ions on *Escherichia coli* and *Staphylococcus aureus,* Q.L. Feng, J. Wu, G. Q. Chen, F.Z. Cui, T.N. Kim, J.O. Kim, 200 John Wiley & Sons, Inc., pp. 662-668.

Mode of Bactericidal Action of Silver Zeolite and Its Comparison with That of Silver Nitrate, Yoshinobu Matsumara, Kuniaki Yoshikata, Shin-ichi Kunisaki, Tetsuaki Tsuchido, Applied and Environmental Microbiology, Jul. 2003, p. 4278-4281, vol. 69, No. 7.

Structural and Antimicrobial Studies of Coordination of Compounds of Phenylalanine and Glycine, Ojo Isaac, International Journal of Chemistry, vol. 4, No. 22, Apr. 2012, p. 49-59.

Role of Silver Ions in Destabilization of the Intermolecular Adhesion Forces Measured by Atomic Force Microscopy in *Staphylococcus epidermidis* Biofilms, K. C. Chaw, M. Manimaran, Francis E. H. Tay, Antimicrobial Agents and Chemotherapy, Dec. 2005, p. 48-4859 Vo. 49, No. 12.

Silver-ion-mediated reactive oxygen species generation affecting bactericidal activity, Hee-Jin Park, Jee Yeon Kim, Jaeeun Kim, Joon-Hee Lee, Ji-Sook Hahn, Man Bock Gu, Jeyong Yoon, Water Research 43 (2009) 1027-1032.

Patent Cooperation Treaty International Notification of Transmittal of The International Search Report and the Written Opinion of the International Searching Authority, international application No. PCT/US2014/015471: mailing date Jul. 4, 2014, 12 pages.

* cited by examiner

ANTIMICROBIAL GLASS ARTICLES AND METHODS OF MAKING AND USING SAME

CROSS-REFERENCE TO RELATED APPLICATIONS

This application claims the benefit of priority under 35 U.S.C. §119 of U.S. Provisional Application Ser. No. 61/763,262 filed on Feb. 11, 2013 the content of which is relied upon and incorporated herein by reference in its entirety.

TECHNICAL FIELD

The present disclosure relates generally to antimicrobial glass articles. More particularly, the various embodiments described herein relate to glass articles having antimicrobial behavior, such that the glass articles exhibit reduced discoloration when exposed to harsh conditions (e.g., elevated temperatures, humidity, oxidizing environments, reducing environments, and/or the like) while maintaining antimicrobial efficacy, as well as to methods of making and using the glass articles.

BACKGROUND

Touch-activated or -interactive devices, such as screen surfaces (e.g., surfaces of electronic devices having user-interactive capabilities that are activated by touching specific portions of the surfaces), have become increasingly more prevalent. In general, these surfaces should exhibit high optical transmission, low haze, and high durability, among other features. As the extent to which the touch screen-based interactions between a user and a device increases, so too does the likelihood of the surface harboring microorganisms (e.g., bacteria, fungi, viruses, and the like) that can be transferred from user to user.

To minimize the presence of microbes on glass, so-called "antimicrobial" properties have been imparted to a variety of glass articles. Such antimicrobial glass articles, regardless of whether they are used as screen surfaces of touch-activated devices or in other applications, have a propensity to discolor for various reasons. For example, one reason includes the presence of reduced Ag due to exposure to elevated temperatures, humidity, reactive environments, and/or the like. These harsh conditions can occur during fabrication or processing of the glass articles, or during ordinary use of the articles. In certain cases, this discoloration can render a glass article unsightly. Further, excessive discoloration ultimately can lead to the glass article becoming unsuitable for its intended purpose.

There accordingly remains a need for technologies that provide antimicrobial glass articles with improved resistance against discoloration when exposed to harsh conditions. It would be particularly advantageous if such technologies did not adversely affect other desirable properties of the surfaces (e.g., optical transmission, haze, strength, scratch resistance, and the like). It is to the provision of such technologies that the present disclosure is directed.

BRIEF SUMMARY

Described herein are various antimicrobial glass articles that have improved resistance to discoloration when exposed to harsh conditions, along with methods for their manufacture and use.

One type of improved antimicrobial glass article includes a glass substrate that has a compressive stress layer or region that extends inward from a surface of the glass substrate to a first depth, and an antimicrobial silver-containing layer or region that extends inward from the surface of the glass substrate to a second depth, such that the glass article experiences substantially no discoloration when exposed to harsh conditions.

This type of antimicrobial glass article can further include an additional layer disposed on the surface of the glass substrate. The additional layer can include a reflection-resistant coating, a glare-resistant coating, fingerprint-resistant coating, smudge-resistant coating, a color-providing composition, an environmental barrier coating, or an electrically conductive coating.

In one or more embodiments, the glass substrate may have a low concentration of nonbridging oxygens (NBOs). A mechanism for the reduction of silver and thus the discoloration due to exposure to harsh conditions, can be related to the concentration of NBOs in the glass substrate. The measure of the concentration of NBOs is proportional to the quantity (alumina mol %–total alkali mol %). In one or more embodiments the antimicrobial glass article may include a glass substrate with a low concentration of NBOs such that the difference between (alumina mol %–total alkali mol %) in the glass substrate may be greater than or equal ($\geq$) to about −1 mol % or, more specifically, greater than or equal ($\geq$) to about 0 mol %.

In certain implementations of this type of improved antimicrobial glass article, a compressive stress of the compressive stress layer can be about 200 megapascals to about 1.2 gigapascals, and/or the depth of the compressive stress layer can be greater than or equal to about 25 micrometers ($\mu m$) and less than or equal to about 100 micrometers ($\mu m$).

In some implementations of this type of improved antimicrobial glass article, the antimicrobial silver-containing region can have an average thickness of less than or equal to about 20 micrometers ($\mu m$). A silver concentration in an outermost portion of such an antimicrobial silver-containing region can be greater than about 5 weight percent and, in some cases, up to about 45 weight percent, based on the total weight of the antimicrobial silver-containing region.

In other implementations of this type of improved antimicrobial glass article, the antimicrobial silver-containing region can have an average thickness of up to about 150 micrometers ($\mu m$) and, in some instances, in a range from about 20 micrometers ($\mu m$) to about 150 micrometers ($\mu m$). A silver concentration in an outermost portion of such an antimicrobial silver-containing region can be up to about 6 weight percent.

The harsh conditions can include temperatures of greater than or equal to about 180 degrees Celsius, relative humidities of greater than or equal to about 50 percent, reducing environments or a combination thereof. For example, the harsh conditions can include polymerization of a fingerprint- and/or smudge-resistant coating on the surface of the glass substrate at elevated temperatures, direct bonding of an adhesive used to adhere the glass substrate to another device, sputtering of a transparent electrode on the surface of the glass substrate, thermal curing of an ink layer on the surface of the glass substrate, plasma cleaning of the surface of the glass substrate, chemical etching of the surface of the glass substrate, annealing of the surface of the glass substrate, chemical cleaning of the surface of the glass substrate, or a combination thereof. In some embodiments, exposure to harsh conditions can include exposure to harsh conditions for about 1.5 hours or more, about 2 hours or more, about 2.5 hours or more, about 3 hours or more, or even about 4 hours or more.

Substantially no discoloration can include a change in optical transmittance of the glass article of less than or equal to about 3 percent relative to an optical transmittance before exposure to the harsh conditions, a change in haze of the glass article of less than or equal to about 5 percent relative to a haze before exposure to the harsh conditions, and/or a change in CIE 1976 color coordinates L*, a*, and b* of the glass article of less than or equal to about ±0.2, ±0.1, and ±0.1, respectively. In some embodiments, the change in CIE 1976 color coordinates L*, a* and b* of the antimicrobial glass article is less than or equal to about ±0.1, ±0.05, ±0.05, respectively.

This type of antimicrobial glass article can exhibit at least a 5 log reduction in a concentration of at least *Staphylococcus aureus, Enterobacter aerogenes*, and *Pseudomonas aeruginosa* bacteria under JIS Z 2801 (2000) testing conditions. This type of antimicrobial glass article can also exhibit at least a 3 log reduction in a concentration of at least *Staphylococcus aureus, Enterobacter aerogenes*, and *Pseudomonas aeruginosa* bacteria under modified JIS Z 2801 (2000) testing conditions, wherein the modified conditions comprise heating the antimicrobial glass article to a temperature of about 23 degrees Celsius to about 37 degrees Celsius at a humidity of about 38 percent to about 42 percent for about 6 hours. This type of antimicrobial glass article can also exhibit ≤2 log reduction in a concentration of at least *Staphylococcus aureus, Enterobacter aerogenes*, and *Pseudomonas aeruginosa* bacteria under modified EPA testing conditions, wherein the modified conditions comprise heating the antimicrobial glass article to a temperature of about 23 degrees Celsius at a humidity of about 38 percent to about 42 percent for about 2 hours.

This type of improved antimicrobial glass article can serve as a portion of a touch-sensitive display screen or cover plate for an electronic device, a non-touch-sensitive component of an electronic device, a surface of a household appliance, a surface of medical equipment, a biological or medical packaging vessel, or a surface of a vehicle component.

One type of method of making an antimicrobial glass article includes providing a glass substrate having a low concentration of nonbridging oxygens, forming a compressive stress layer that extends inward from a surface of the glass substrate to a first depth, and forming an antimicrobial silver-containing region that extends inward from the surface of the glass substrate to a second depth, such that the glass article undergoes substantially no discoloration when exposed to harsh conditions.

In some cases, the method can also include forming an additional layer on at least a portion of the surface of the substrate, wherein the additional layer comprises a reflection-resistant coating, a glare-resistant coating, fingerprint-resistant coating, smudge-resistant coating, a color-providing composition, an environmental barrier coating, or an electrically conductive coating.

In some cases, the step of forming the compressive stress layer and the step of forming the antimicrobial silver-containing region occur simultaneously.

It is to be understood that both the foregoing brief summary and the following figures and detailed description describe various embodiments and are intended to provide an overview or framework for understanding the nature and character of the claimed subject matter.

DETAILED DESCRIPTION

Figure 1:
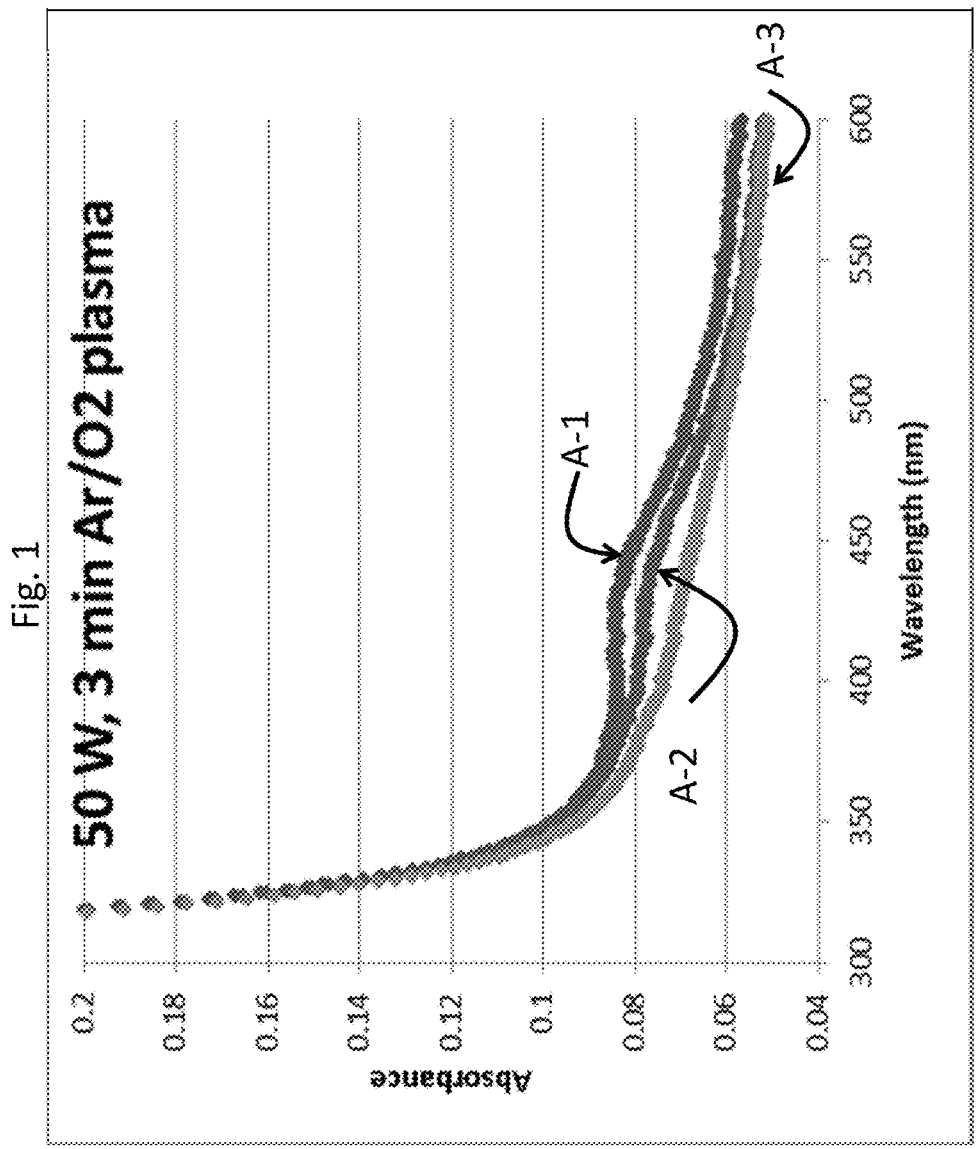
FIG. 1 is a graph illustrating the absorbance of a glass article over a wavelength range, according to one or more embodiments.

Throughout this description, various components may be identified having specific values or parameters. These items, however, are provided as being exemplary of the present disclosure. Indeed, the exemplary embodiments do not limit the various aspects and concepts, as many comparable parameters, sizes, ranges, and/or values may be implemented. Similarly, the terms "first," "second," "primary," "secondary," "top," "bottom," "distal," "proximal," and the like, do not denote any order, quantity, or importance, but rather are used to distinguish one element from another. Further, the terms "a," "an," and "the" do not denote a limitation of quantity, but rather denote the presence of "at least one" of the referenced item.

Described herein are various antimicrobial glass articles that have improved resistance to discoloration when exposed to harsh conditions (i.e., during manufacture and/or use of the articles), along with methods for their manufacture and use. The term "antimicrobial" refers herein to the ability to kill or inhibit the growth of more than one species of more than one type of microbe (e.g., bacteria, viruses, fungi, and the like). In general, the improved articles and methods described herein involve the use of a glass substrate that has a low concentration of nonbridging oxygens (NBOs). As used herein, the term "nonbridging oxygens" is intended to refer to those oxygen atoms within the glass that bear a negative charge that can be compensated by a vicinal positively charged ion. For example, where silicon is bonded to four oxygen atoms and where the bond between the silicon atom and one of the oxygen atoms is broken, that oxygen atom bears a negative charge, which may be compensated by an alkali atom (e.g., Na). This is in contrast to those oxygen atoms within the glass that are covalently bonded to other atoms and do not bear a negative charge (such oxygen atoms being termed "bridging oxygens"). One way to determine the concentration of NBOs includes subtracting the sum of the concentrations, in mole percent (mol %), of all alkali metal oxides from the concentration, in mol %, of aluminum oxide. That is, NBO concentration is proportional to ($Al_2O_3$ (mol %)−(Σ alkali metal oxides (mol %)). It is important to note that, because of this particular NBO concentration calculation, NBO concentration values can be negative. Thus, in some implementations of the glass articles, the concentration of NBOs will be less than zero. Where the difference $Al_2O_3$ (mol %)−(Σ alkali metal oxides (mol %)) equals zero or a positive number, then there are no NBOs present. Where the difference $Al_2O_3$ (mol %)−(Σ alkali metal oxides (mol %)) equals a negative number, that negative number indicates the presence of NBOs.

Discoloration in antimicrobial glass articles occurs when NBOs present in a glass substrate provide an electron to an $Ag^+$ ion, thus reducing the $Ag^+$ ion to $Ag^0$. $Ag^0$ provides poor antimicrobial activity as compared to $Ag^+$. Reduced $Ag^0$ also shows a distinct plasmon resonance peak at 430 nm which appears as a color change to the eye of an observer. This cause of Ag reduction, and thus discoloration, due to the presence of NBOs should be distinguished from other causes of discoloration. Electrons may be present or formed in the glass substrate from other sources, such as exposure to ultraviolet light, which are unrelated to the amount of NBOs present in the glass substrate. These electrons may cause Ag+ ions or other metal ions present in the glass to reduce and thus, cause discoloration of the glass substrate. This type of UV-induced discoloration can be distinguished from the discoloration attributable to the presence of NBOs.

The improved antimicrobial glass articles described herein generally include a glass substrate that has a compressive stress layer or region that extends inward from a surface of the glass substrate to a first depth, and an antimicrobial silver-containing layer or region that extends inward from a surface of the glass substrate to a second depth, such that the glass article experiences little-to-no discoloration when exposed to harsh conditions. Throughout this specification, the term "compressive stress layer" shall be used to refer to the layer or region of compressive stress, and the term "antimicrobial silver-containing region" shall be used to refer to the layer or region containing the antimicrobial silver species. This usage is for convenience only, and is not intended to provide a distinction between the terms "region" or "layer" in any way.

In one or more embodiments, the glass substrate may have a low concentration of NBOs, The choice of glass used for the glass substrate is not limited to a particular composition, as improved resistance to discoloration can be obtained using a variety of glass compositions that have a low concentration of NBOs, as defined above. For example, the composition chosen can be any of a wide range of silicate, borosilicate, aluminosilicate, or boroaluminosilicate glass compositions, which optionally can comprise one or more alkali and/or alkaline earth modifiers.

By way of illustration, one family of compositions includes those having at least one of aluminum oxide or boron oxide and at least one of an alkali metal oxide or an alkali earth metal oxide, wherein −15 mol %≤($R_2O$+R'O—$Al_2O_3$—$ZrO_2$)—$B_2O_3$≤4 mol %, where R can be Li, Na, K, Rb, and/or Cs, and R' can be Mg, Ca, Sr, and/or Ba. One subset of this family of compositions includes from about 62 mol % to about 70 mol % $SiO_2$; from 0 mol % to about 18 mol % $Al_2O_3$; from 0 mol % to about 10 mol % $B_2O_3$; from 0 mol % to about 15 mol % $Li_2O$; from 0 mol % to about 20 mol % $Na_2O$; from 0 mol % to about 18 mol % $K_2O$; from 0 mol % to about 17 mol % MgO; from 0 mol % to about 18 mol % CaO; and from 0 mol % to about 5 mol % $ZrO_2$. Such glasses are described more fully in U.S. patent application Ser. No. 12/277,573 by Matthew J. Dejneka et al., entitled "Glasses Having Improved Toughness And Scratch Resistance," filed Nov. 25, 2008, and claiming priority to U.S. Provisional Patent Application No. 61/004,677, filed on Nov. 29, 2008, the contents of which are incorporated herein by reference in their entireties as if fully set forth below.

Another illustrative family of compositions includes those having at least 50 mol % $SiO_2$ and at least one modifier selected from the group consisting of alkali metal oxides and alkaline earth metal oxides, wherein [($Al_2O_3$ (mol %)+$B_2O_3$ (mol %))/(Σ alkali metal modifiers (mol %))]>1. One subset of this family includes from 50 mol % to about 72 mol % $SiO_2$; from about 9 mol % to about 17 mol % $Al_2O_3$; from about 2 mol % to about 12 mol % $B_2O_3$; from about 8 mol % to about 16 mol % $Na_2O$; and from 0 mol % to about 4 mol % $K_2O$. Such glasses are described in more fully in U.S. patent application Ser. No. 12/858,490 by Kristen L. Barefoot et al., entitled "Crack And Scratch Resistant Glass and Enclosures Made Therefrom," filed Aug. 18, 2010, and claiming priority to U.S. Provisional Patent Application No. 61/235,767, filed on Aug. 21, 2009, the contents of which are incorporated herein by reference in their entireties as if fully set forth below.

Yet another illustrative family of compositions includes those having $SiO_2$, $Al_2O_3$, $P_2O_5$, and at least one alkali metal oxide ($R_2O$), wherein 0.75≤[($P_2O_5$ (mol %)+$R_2O$ (mol %))/$M_2O_3$ (mol %)]≤1.2, where $M_2O_3$=$Al_2O_3$+$B_2O_3$. One subset of this family of compositions includes from about 40 mol % to about 70 mol % $SiO_2$; from 0 mol % to about 28 mol % $B_2O_3$; from 0 mol % to about 28 mol % $Al_2O_3$; from about 1 mol % to about 14 mol % $P_2O_5$; and from about 12 mol % to about 16 mol % $R_2O$. Another subset of this family of compositions includes from about 40 to about 64 mol % $SiO_2$; from 0 mol % to about 8 mol % $B_2O_3$; from about 16 mol % to about 28 mol % $Al_2O_3$; from about 2 mol % to about 12 mol % $P_2O_5$; and from about 12 mol % to about 16 mol % $R_2O$. Such glasses are described more fully in U.S. patent application Ser. No. 13/305,271 by Dana C. Bookbinder et al., entitled "Ion Exchangeable Glass with Deep Compressive Layer and High Damage Threshold," filed Nov. 28, 2011, and claiming priority to U.S. Provisional Patent Application No. 61/417,941, filed Nov. 30, 2010, the contents of which are incorporated herein by reference in their entireties as if fully set forth below.

Yet another illustrative family of compositions includes those having at least about 4 mol % $P_2O_5$, wherein ($M_2O_3$ (mol %)/$R_xO$ (mol %))<1, wherein $M_2O_3$=$Al_2O_3$+$B_2O_3$, and wherein $R_xO$ is the sum of monovalent and divalent cation oxides present in the glass. The monovalent and divalent cation oxides can be selected from the group consisting of $Li_2O$, $Na_2O$, $K_2O$, $Rb_2O$, $Cs_2O$, MgO, CaO, SrO, BaO, and ZnO. One subset of this family of compositions includes glasses having 0 mol % $B_2O_3$. Such glasses are more fully described in U.S. Provisional Patent Application No. 61/560,434 by Timothy M. Gross, entitled "Ion Exchangeable Glass with High Crack Initiation Threshold," filed Nov. 16, 2011, the contents of which are incorporated herein by reference in their entirety as if fully set forth below.

Still another illustrative family of compositions includes those having $Al_2O_3$, $B_2O_3$, alkali metal oxides, and contains boron cations having three-fold coordination. When ion exchanged, these glasses can have a Vickers crack initiation threshold of at least about 30 kilograms force (kgf). One subset of this family of compositions includes at least about 50 mol % $SiO_2$; at least about 10 mol % $R_2O$, wherein $R_2O$ comprises $Na_2O$; $Al_2O_3$, wherein −0.5 mol % ≤ $Al_2O_3$ (mol %) − $R_2O$ (mol %) ≤ 2 mol %; and $B_2O_3$, and wherein $B_2O_3$ (mol %) − ($R_2O$ (mol %) − $Al_2O_3$ (mol %)) ≥ 4.5 mol %. Another subset of this family of compositions includes at least about 50 mol % $SiO_2$, from about 9 mol % to about 22 mol % $Al_2O_3$; from about 4.5 mol % to about 10 mol % $B_2O_3$; from about 10 mol % to about 20 mol % $Na_2O$; from 0 mol % to about 5 mol % $K_2O$; at least about 0.1 mol % MgO and/or ZnO, wherein 0 ≤ MgO+ZnO ≤ 6 mol %; and, optionally, at least one of CaO, BaO, and SrO, wherein 0 mol % ≤ CaO+SrO+BaO ≤ 2 mol %. Such glasses are more fully described in U.S. Provisional Patent Application No. 61/653,485 by Matthew J. Dejneka et al., entitled "Ion Exchangeable Glass with High Damage Resistance," filed May 31, 2012, the contents of which are incorporated herein by reference in their entirety as if fully set forth below.

In general, the concentration of NBOs, as defined above, in the glass articles can be, in mol %, ≥ to about −1, ≥ to about −0.9, ≥ to about −0.8, ≥ to about −0.7, ≥ to about −0.6, ≥ to about −0.5, ≥ to about −0.4, ≥ to about −0.3, ≥ to about −0.2, ≥ to about −0.1, ≥ to about 0, ≥ to about 0.1, ≥ to about 0.2, ≥ to about 0.3, ≥ to about 0.4, ≥ to about 0.5, ≥ to about 0.6, ≥ to about 0.7, ≥ to about 0.8, ≥ to about 0.9 ≥ to about 1. In some embodiments, the NBO concentration may be in the range from about −1 mol % to about 20 mol %, from about −1 mol % to about 15 mol %, from about −1 mol % to about 10 mol %, from about −1 mol % to about 5 mol %, from about −1 mol % to about 4 mol %, from about −1 mol % to about 3 mol %, from about −1 mol % to about 2 mol %, from about −1 mol % to about 1 mol %, from about −1 mol % to about 0.75 mol %, from about −1 mol % to about 0.5 mol %, from about −1 mol % to about 0.25 mol %, from about −1 mol % to about 0 mol %, from about −0.75 mol % to about 1 mol %, from about −0.5 mol % to about 1 mol %, from about −0.25 mol % to about 1 mol %, from about −0.25 mol % to about 0.25 mol % and all ranges and sub-ranges therebetween.

The glass substrate can adopt a variety of physical forms. That is, from a cross-sectional perspective, the substrate can be flat or planar, or it can be curved and/or sharply-bent. Similarly, it can be a single unitary object, or a multi-layered structure or a laminate.

Regardless of its composition or physical form, the glass substrate will include a layer or region under compressive stress that extends inward from a surface of the glass substrate to a specific depth therein. This compressive stress layer can be formed from a strengthening process (e.g., by thermal tempering, chemical ion-exchange, or like processes). The amount of compressive stress (CS) and the depth of the compressive stress layer (DOL) can be varied based on the particular use for the glass article, with the proviso that the CS and DOL should be limited such that a tensile stress created within the glass as a result of the compressive stress layer does not become so excessive as to render the glass article frangible.

In addition, the glass substrate will include an antimicrobial silver-containing layer or region that extends inward from a surface of the glass substrate to a specific depth therein. The antimicrobial silver-containing region comprises cationic monovalent silver ($Ag^+$) in an amount effective to impart antimicrobial behavior to the glass article. In general, the antimicrobial silver-containing region, like the compressive stress layer, extends inward from the surface of the glass substrate. Thus the antimicrobial silver-containing region at least partially overlaps with the compressive stress layer. In some embodiments, the depth of the compressive stress layer is greater than the depth of the antimicrobial silver-containing region. In other embodiments, the depth of the compressive stress layer and the depth of the antimicrobial silver-containing region are about the same. The depth of the antimicrobial silver-containing region (DOR) may be generally be limited so as to avoid visible coloration in the glass article and to maximize the antimicrobial efficacy of the cationic silver within the glass substrate.

In certain implementations, the antimicrobial glass articles can include an additional layer disposed on the surface of the glass substrate. The optional additional layer(s) can be used to provide additional features to the antimicrobial glass article (e.g., reflection resistance or anti-reflection properties, glare resistance or anti-glare properties, fingerprint resistance or anti-fingerprint properties, smudge resistance or anti-smudge properties, color, opacity, environmental barrier protection, electronic functionality, and/or the like). Materials that can be used to form the optional additional layer(s) generally are known to those skilled in the art to which this disclosure pertains.

Methods of making the above-described articles generally include the steps of providing a glass substrate having a low concentration of NBOs, forming a compressive stress layer that extends inward from a surface of the glass substrate to a first depth, and forming an antimicrobial silver-containing region that extends inward from the surface of the glass substrate to a second depth, such that the as-produced glass article experiences little-to-no discoloration when exposed to harsh conditions. In those embodiments where the optional additional layer is implemented, the methods generally involve an additional step of forming the additional layer on at least a portion of the surface of the substrate.

The selection of materials used in the glass substrates and optional additional layers can be made based on the particular application desired for the final glass article. In general, however, the specific materials will be chosen from those described above.

Provision of the glass substrate having a low concentration of NBOs can involve selection of a glass object as-manufactured, or it can entail subjecting the as-manufactured glass object to a treatment in preparation for any of the subsequent steps. Examples of such treatments include physical or chemical cleaning, physical or chemical etching, physical or chemical polishing, annealing, shaping, and/or the like.

Once the glass substrate having a low concentration of NBOs has been selected and/or prepared, the compressive stress layer and/or the antimicrobial silver-containing region can be formed therein. That is, the compressive stress layer can be formed before, after, or simultaneously with the antimicrobial silver-containing region.

Formation of the compressive stress layer can be accomplished in a variety of ways, of which thermal tempering and chemical ion exchange are the most common. Similarly, the antimicrobial silver-containing region can be formed in a variety of ways, of which chemical diffusion (which optionally can be accompanied by the exchange of another cation out from the glass) of cationic silver from a silver-containing medium (e.g., paste, dispersion, ion exchange bath of molten salts, or the like) is the most common.

By way of example, one exemplary implementation of a method where the compressive stress layer is formed before the antimicrobial silver-containing region entails immersing the glass into a molten $KNO_3$ bath to impart the compressive stress via ion exchange followed by immersing the strengthened glass into a $AgNO_3$-containing molten salt bath to ion exchange $Ag^+$ into the glass.

By way of another example, one exemplary implementation of a method where the compressive stress layer is formed after the antimicrobial silver-containing region entails immersing the glass into a $AgNO_3$-containing molten salt bath to ion exchange $Ag^+$ into the glass followed by immersing the Ag-containing glass into a molten $KNO_3$ bath to impart the compressive stress via ion exchange.

By way of still another example, one exemplary implementation of a method where the compressive stress layer and the antimicrobial silver-containing region are formed simultaneously entails immersing the glass into a molten salt bath comprising both $KNO_3$ and $AgNO_3$ to ion exchange $K^+$ and $Ag^+$ into the glass together.

After the compressive stress layer and the antimicrobial silver-containing region are formed, if desired, the optional additional layer(s) can be disposed on the surface of the glass substrate. Depending on the materials chosen, these coatings can be formed using a variety of techniques. For example, the optional additional layer(s) can be fabricated independently using any of the variants of chemical vapor deposition (CVD) (e.g., plasma-enhanced CVD, aerosol-assisted CVD, metal organic CVD, and the like), any of the variants of physical vapor deposition (PVD) (e.g., ion-assisted PVD, pulsed laser deposition, cathodic arc deposition, sputtering, and the like), spray coating, spin-coating, dip-coating, inkjetting, sol-gel processing, or the like. Such processes are known to those skilled in the art to which this disclosure pertains.

It should be noted that between any of the above-described steps, the glass substrate can undergo a treatment in preparation for any of the subsequent steps. As described above, examples of such treatments include physical or chemical cleaning, physical or chemical etching, physical or chemical polishing, annealing, shaping, and/or the like.

Once the glass article is formed, it can be used in a variety of applications where the article will come into contact with undesirable microbes. These applications encompass touch-sensitive display screens or cover plates for various electronic devices (e.g., cellular phones, personal data assistants, computers, tablets, global positioning system navigation devices, and the like), non-touch-sensitive components of electronic devices, surfaces of household appliances (e.g., refrigerators, microwave ovens, stovetops, oven, dishwashers, washers, dryers, and the like), medical equipment, biological or medical packaging vessels, and vehicle components, just to name a few devices.

Given the breadth of potential uses for the improved antimicrobial glass articles described herein, it should be understood that the specific features or properties of a particular article will depend on the ultimate application therefor or use thereof. The following description, however, will provide some general considerations.

There is no particular limitation on the average thickness of the glass substrate contemplated herein. In many exemplary applications, however the average thickness will be less than or equal to about 15 millimeters (mm). If the antimicrobial glass article is to be used in applications where it may be desirable to optimize thickness for weight, cost, and strength characteristics (e.g., in electronic devices, or the like), then even thinner substrates (e.g., less than or equal to about 5 mm) can be used. By way of example, if the antimicrobial glass article is intended to function as a cover for a touch screen display, then the substrate can exhibit an average thickness of about 0.02 mm to about 2.0 mm.

While the ultimate limit on the CS and DOL is the avoidance of rendering the glass article frangible, the average DOL of the compressive stress layer generally will be less than about one-third of the thickness of the glass substrate. In most applications, however, the average DOL will be greater than or equal to about 25 micrometers ($\mu m$) and less than or equal to about 100 micrometers ($\mu m$). Similarly, the average CS across the depth of the compressive stress layer generally will be between about 200 megapascals (MPa) and about 1.2 gigapascals (GPa). In most applications, the average CS will be greater than 400 MPa.

As stated above, the thickness of the antimicrobial silver-containing region can be limited so as to avoid visible coloration in the glass article and to maximize the antimicrobial efficacy of the cationic silver within the glass substrate. The average thickness of the antimicrobial silver-containing region may be less than the DOL of the compressive stress layer. In some embodiments, as with the DOL of the compressive stress layer, the average thickness of the antimicrobial silver-containing region in one or more embodiments, may be less than about one-third of the thickness of the glass substrate. In some alternative embodiments, the average thickness of the antimicrobial silver-containing region may be up to about 100 micrometers ($\mu m$), up to about 150 micrometers ($\mu m$), up to about 300 micrometers ($\mu m$), or up to the entire thickness of the glass substrate. The exact thickness, however, will vary depending on how the antimicrobial silver-containing region is formed.

For example, if the antimicrobial silver-containing region is formed before or after the compressive stress layer, and both are formed via chemical ion exchange, then the average thickness of the antimicrobial silver-containing region generally may be less than or equal to about 20 micrometers ($\mu m$). In many such cases, the average thickness of the antimicrobial silver-containing region may be less than or equal to about 10 micrometers ($\mu m$), less than or equal to about 5 micrometers ($\mu m$), less than or equal to about 3 micrometers ($\mu m$), less than or equal to about 2 micrometers ($\mu m$), less than or equal to about 1 micrometers ($\mu m$), or less than or equal to about 0.2 micrometers ($\mu m$). The minimum average thickness of the antimicrobial silver-containing region may be about 10 nanometers (nm). In some embodiments, the average thickness of the antimicrobial silver-containing region is in the range from about 5 micrometers ($\mu m$) to about 8 micrometers ($\mu m$) or from about 2 micrometers ($\mu m$) to about 5 micrometers ($\mu m$). Within this antimicrobial silver-containing region, silver concentrations at the outermost portion of this region (which includes about the outermost 50 nanometers (nm)) of up to about 45 weight percent (wt %), based on the total weight of this portion of the region, can be attained.

In contrast, if the antimicrobial silver-containing region is formed at the same time as the compressive stress layer, and both are formed via chemical ion exchange, then the average thickness of the antimicrobial silver-containing region generally may be up to about 150 micrometers ($\mu m$). In some embodiments, the average thickness of the antimicrobial silver-containing region may be in the range from about 20 micrometers ($\mu m$) to about 100 micrometers ($\mu m$), from about 20 micrometers ($\mu m$) to about 150 micrometers ($\mu m$) or from about 20 micrometers ($\mu m$) to about 300 micrometers ($\mu m$). Within this region, silver concentrations at the outermost portion of this region (which includes about the outermost 50 nanometers (nm)) of up to about 10 wt %, 9 wt %, 8 wt %, 7 wt %, 6 wt %, 5 wt %, 4 wt % or 3 wt %, based on the total weight of this portion of the region, can be attained.

When an optional additional layer is used, the average thickness of such a layer will depend on the function it serves. For example if a glare- and/or reflection-resistant layer is implemented, the average thickness of such a layer should be less than or equal to about 200 nanometers (nm). Coatings that have an average thickness greater than this could scatter light in such a manner that defeats the glare and/or reflection resistance properties. Similarly, if a fingerprint- and/or smudge-resistant layer is implemented, the average thickness of such a layer should be less than or equal to about 100 nanometers (nm).

In general, the optical transmittance of the antimicrobial glass article will depend on the type of materials chosen. For example, if a glass substrate is used without any pigments added thereto and/or any optional additional layers are sufficiently thin, the article can have a transparency over the entire visible spectrum of at least about 85%. In certain cases where the antimicrobial glass article is used in the construction of a touch screen for an electronic device, for example, the transparency of the antimicrobial glass article can be at least about 90% over the visible spectrum. In situations where the glass substrate comprises a pigment (or is not colorless by virtue of its material constituents) and/or any optional additional layers are sufficiently thick, the transparency can diminish, even to the point of being opaque across the visible spectrum. Thus, there is no particular limitation on the optical transmittance of the antimicrobial glass article itself.

Like transmittance, the haze of the antimicrobial glass article can be tailored to the particular application. As used herein, the terms "haze" and "transmission haze" refer to the percentage of transmitted light scattered outside an angular cone of ±4.0° in accordance with ASTM procedure D1003, the contents of which are incorporated herein by reference in their entirety as if fully set forth below. For an optically smooth surface, transmission haze is generally close to zero. In those situations when the antimicrobial glass article is used in the construction of a touch screen for an electronic device, the haze of the article can be less than or equal to about 5%, or more specifically, less than or equal to about 1%.

Regardless of the application or use, the antimicrobial glass articles described herein offer improved discoloration resistance to harsh conditions relative to existing antimicrobial glass articles. As used herein, the term "harsh conditions" refer to elevated temperatures, high relative humidities, reactive environments, and/or the like. For example, these can include temperatures of greater than about 180 degrees Celsius (° C.), relative humidities of greater than 50 percent (%), reducing environments, and/or the like. Such harsh conditions can be generated during manufacture and/or ordinary use of the antimicrobial glass articles. By way of illustration of the former, harsh conditions can be generated during the formation of any optional additional layers disposed on the surface of the glass substrate (e.g., during polymerization of a fingerprint- and/or smudge-resistant coating on the surface of the glass substrate at elevated temperatures, during direct bonding of adhesives used to adhere the glass substrate to another device, during sputtering of a transparent electrode, during thermal curing of an ink layer, and/or the like), during any intermediate treatment steps (e.g., during plasma cleaning, during chemical etching, during annealing, during chemical cleaning, and/or the like), or the like. Thus, in certain implementations, the antimicrobial glass articles exhibit improved discoloration resistance relative to existing antimicrobial glass articles when exposed to any of the above conditions.

While discoloration resistance can appear to be a qualitative and potentially subjective characterization, there are a number of quantifiable indications of discoloration resistance, examples of which will now be described.

One quantifiable indication of this improved resistance to discoloration can be seen in the change in the optical transmittance that is observed over time. This change can be measured after the formation of the antimicrobial silver-containing region but before the glass article is exposed to any harsh conditions and after the glass article is exposed to harsh conditions. In general, the optical transmittance of the glass articles described herein can be substantially similar both before and after exposure to harsh conditions. In certain implementations, the change in the transmittance of the glass articles described herein after exposure to harsh conditions can be about ±3%. In other implementations, the change in the transmittance of the glass articles described herein after exposure to harsh conditions can be about ±0.5%.

Another quantifiable indication of improved resistance to discoloration is the change in absorbance at about 430 nm, which corresponds to the plasmon resonance associated with the formation of metallic silver nanoparticles (from cationic silver species) in the glass substrate, over time. This change can be measured after the formation of the antimicrobial silver-containing region but before the glass article is exposed to any harsh conditions and after the glass article is exposed to harsh conditions. In general, the absorbance at about 430 nm of the glass articles described herein can be substantially similar both before and after exposure to harsh conditions. In certain implementations, the change in the absorbance at about 430 nm of the glass articles described herein after exposure to harsh conditions can be about ±25%. In other implementations, the change in the absorbance at about 430 nm of the glass articles described herein after exposure to harsh conditions can be about ±10%.

Yet another quantifiable indication of the improved resistance to discoloration is the change in haze that is observed over time. This change can be measured after the formation of the antimicrobial silver-containing region but before the glass article is exposed to any harsh conditions and after the glass article is exposed to harsh conditions. In general, the overall haze of the glass articles described herein after exposure to harsh conditions can be substantially similar to the haze of the as-produced glass articles. In certain implementations, the change in the haze of the glass articles described herein after exposure to harsh conditions can be about ±5%. In other implementations, the change in the haze of the glass articles described herein after exposure to harsh conditions can be about ±2%.

Still another quantifiable indication of the improved resistance to discoloration is the change in CIE 1976 color space coordinates that is observed over time. This change can be measured after the formation of the antimicrobial silver-containing region but before the glass article is exposed to any harsh conditions and after the glass article is exposed to harsh conditions. In general, the individual coordinates (i.e., $L^*$, $a^*$, and $b^*$) of the glass articles described herein after exposure to harsh conditions can be substantially similar to the individual coordinates of the as-produced glass articles. In certain implementations, the change in the $L^*$, $a^*$, and $b^*$ coordinates of the glass articles described herein after exposure to harsh conditions can be about ±0.2, ±0.1, and ±0.1, respectively. In other implementations, the change in the $L^*$, a*, and b* coordinates of the glass articles described herein after exposure to harsh conditions can be about ±0.1, ±0.05, and ±0.05, respectively.

The antimicrobial activity and efficacy of the antimicrobial glass articles described herein can be quite high. The antimicrobial activity and efficacy can be measured in accordance with Japanese Industrial Standard JIS Z 2801 (2000), entitled "Antimicrobial Products-Test for Antimicrobial Activity and Efficacy," the contents of which are incorporated herein by reference in their entirety as if fully set forth below. Under the "wet" conditions of this test (i.e., about 37° C. and greater than 90% humidity for about 24 hours), the antimicrobial glass articles described herein can exhibit at least a 5 log reduction in the concentration (or a kill rate of 99.999%) of at least *Staphylococcus aureus, Enterobacter aerogenes*, and *Pseudomonas aeruginosa* bacteria. In certain implementations, the antimicrobial glass articles described herein can exhibit at least a 7 log reduction in the concentration of any bacteria to which it is exposed under these testing conditions.

In scenarios where the wet testing conditions of JIS Z 2801 do not reflect actual use conditions of the antimicrobial glass articles described herein (e.g., when the glass articles are used in electronic devices, or the like), the antimicrobial activity and efficacy can be measured using "drier" conditions. For example, the glass articles can be tested between about 23 and about 37° C. and at about 38 to about 42% humidity for about 24 hours. Specifically, 5 control samples and 5 test samples can be used, wherein each sample has a specific inoculum composition and volume applied thereto, with a sterile coverslip applied to the inoculated samples to ensure uniform spreading on a known surface area. The covered samples can be incubated under the conditions described above, dried for about 6 to about 24 hours, rinsed with a buffer solution, and enumerated by culturing on an agar plate, the last two steps of which are similar to the procedure employed in the JIS Z 2801 test. Using this test, the antimicrobial glass articles described herein can exhibit at least a 1 log reduction in the concentration (or a kill rate of 90%) of at least *Staphylococcus aureus* bacteria and at least a 2 log reduction in the concentration (or a kill rate of 99.99%) of at least *Enterobacter aerogenes*, and *Pseudomonas aeruginosa* bacteria. In certain implementations, the antimicrobial glass articles described herein can exhibit at least a 3 log reduction in the concentration of any bacteria to which it is exposed under these testing conditions.

In other scenarios where the wet testing conditions of JIS Z 2801 do not reflect actual use conditions of the antimicrobial glass articles described herein (e.g., when the glass articles are used in electronic devices, or the like), the antimicrobial activity and efficacy can be measured using "dry" conditions. These conditions described herein are collectively referred to herein as a "Dry Test". The antimicrobial glass articles may exhibit at least a 1 log reduction in the concentration (or a kill rate of 90%) or even at least a 2 log reduction in the concentration (or kill rate of 99%) of at least *Staphylococcus aureus, Enterobacter aerogenes*, and *Pseudomonas aeruginosa* bacteria when tested under the Dry Test, which is described in U.S. Provisional Patent Application No. 61/908,401, which is hereby incorporated by reference in its entirety as if fully set forth below. In a specific embodiment that might be particularly advantageous for applications such as touch accessed or operated electronic devices, an antimicrobial glass article is formed from a chemically strengthened (ion exchanged) alkali aluminosilicate flat glass sheet. The average thickness of the glass sheet is less than or equal to about 1 mm, the average DOL of the ion exchanged compressive stress layer on each major surface of the glass sheet will be about 40 micrometers (μm) to about 100 micrometers (μm), and the average CS across the depth of the compressive stress layer on each major surface will be about 400 MPa to about 1.1 GPa. The average thickness of the antimicrobial silver-containing region, which is formed by a second ion exchange step that occurs after compressive stress layer is formed, will be about 500 nanometers (nm) to about 10 micrometers (μm). A silver concentration of about 30 wt % to about 40 wt % can be attained in the outermost (i.e., closest to the glass substrate surface) 50 nm of the antimicrobial silver-containing region, based on the total weight of this portion of the antimicrobial silver-containing region. This antimicrobial glass article can have an initial optical transmittance of at least about 90% across the visible spectrum and a haze of less than 1%.

In certain cases, one of the major surfaces of the glass sheet can have an anti-reflection coating and/or an anti-fingerprint coating disposed thereon. After deposition of the anti-reflection coating and/or the anti-fingerprint coating (which can involve temperatures of greater than 200° C., relative humidities of greater than 80%, and exposure to plasma cleaning steps before and/or after deposition), the antimicrobial glass article can have an optical transmittance of at least about 90% across the visible spectrum and a haze of less than 1%. In addition, the change in the L*, a*, and b* coordinates of the glass article after deposition of the anti-reflection coating and/or the anti-fingerprint coating (relative to the uncoated article) can be less than about ±0.15, ±0.08, and ±0.08, respectively. Such an antimicrobial glass article can be used in the fabrication of a touch screen display for an electronic device, offering desirable strength, optical properties, antimicrobial behavior, and resistance to discoloration. In addition, such an antimicrobial glass article can exhibit at least a 5 log reduction in the concentration any bacteria to which it is exposed under the testing conditions of JIS Z 2801.

In another specific embodiment that might be particularly advantageous for applications such as touch accessed or operated electronic devices, an antimicrobial glass article is formed from a chemically strengthened (ion exchanged) alkali aluminosilicate flat glass sheet. The average thickness of the glass sheet is less than or equal to about 1 mm, the average DOL of the ion exchanged compressive stress layer on each major surface of the glass sheet will be about 40 micrometers (μm) to about 100 micrometers (μm), and the average CS across the depth of the compressive stress layer on each major surface will be about 500 MPa to about 1.2 GPa. The average thickness of the antimicrobial silver-containing region, which is formed at the same time that the compressive stress layer is formed (e.g., by including about 0.1 wt % to about 1 wt % $AgNO_3$ in the chemical strengthening molten salt bath), will be about 25 micrometers (μm) to about 110 micrometers (μm). A silver concentration of about 1 wt % to about 5 wt % can be attained in the outermost (i.e., closest to the glass substrate surface) 50 nm of the antimicrobial silver-containing region, based on the total weight of this portion of the antimicrobial silver-containing region. This antimicrobial glass article can have an initial optical transmittance of at least about 90% across the visible spectrum and a haze of less than 1%.

In certain cases, one of the major surfaces of the glass sheet can have an anti-reflection coating and/or an anti-fingerprint coating disposed thereon. After deposition of the anti-reflection coating and/or the anti-fingerprint coating (which can involve temperatures of greater than 180° C., relative humidities of greater than 50%, and exposure to plasma cleaning steps before and/or after deposition), the antimicrobial glass article can have an optical transmittance of at least about 90% across the visible spectrum and a haze of less than 1%. In addition, the change in the L*, a*, and b* coordinates of the glass article after deposition of the anti-reflection coating and/or the anti-fingerprint coating (relative to the uncoated article) can be less than about ±0.1, ±0.06, and ±0.06, respectively. Such an antimicrobial glass article can be used in the fabrication of a touch screen display for an electronic device, offering desirable strength, optical properties, antimicrobial behavior, and resistance to discoloration. In addition, such an antimicrobial glass article can exhibit at least a 5 log reduction in the concentration any bacteria to which it is exposed under the testing conditions of JIS Z 2801.

EXAMPLES

Various embodiments will be further clarified by the following examples.

Example 1

Figure 2:
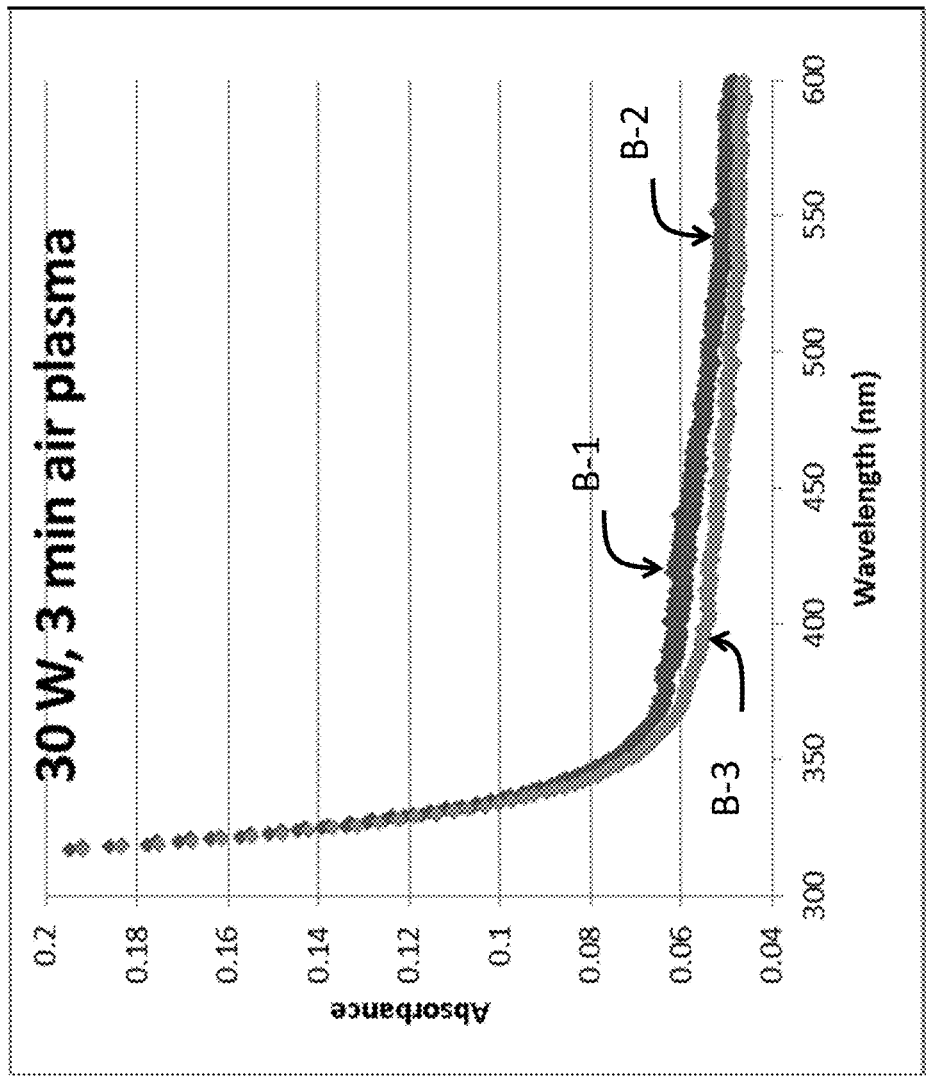
FIG. 2 is a graph illustrating the absorbance of a glass article over a wavelength range, according to one or more embodiments.

Six glass substrates having identical glass compositions that included an NBO amount of about −0.35 mol % were formed and subjected to chemical strengthening in a molten $KNO_3$ bath to impart a compressive stress in each glass substrate, via ion exchange. The six strengthened glass substrates were then immersed a $AgNO_3$-containing molten salt bath to ion exchange $Ag^+$ into the glass substrate, for the same period of time, as shown in Table 1. The resulting glass articles had a $Ag_2O$ content of about 20-28 wt % as measured by the analytical technique of EMP (electron microprobe) over a region of the glass substrates from the surface of the glass substrate to a depth of about 50 nm to about 80 nm into the glass substrate. Examples A1, A2 and A3 were exposed to a mix process gas $Ar/O_2$ and plasma generated at 50 W for about 3 minutes and Examples B1, B2 and B3 were exposed to air as the process gas and plasma generated at 30 W for about 3 minutes. The absorbance of the thus treated Examples A1-A3 and B1-B3 was measured and shown in the graphs of FIGS. 1 and 2. FIG. 1 shows a surface plasmon resonance absorption in the range from about 420 nm to about 430 nm of the spectrum, indicating the reduction of $(Ag^+)_n$ to $(Ag^0)_m$ and the presence of reduced Ag-nanoparticles. FIG. 2 shows only a very slight peak at the same spectrum range and thus illustrates that coloration is dependent on the conditions to which the glass articles are exposed. Where the conditions are harsher (e.g., plasma generated at a higher power), the discoloration will be more noticeable or severe due to the increased amount of reduced Ag-nanoparticles. FIGS. 1 and 2 also illustrate that the amount of $Ag^+$ ions in the glass articles also plays a role in the amount of discoloration. In FIG. 1, Example A1 exhibited the largest peak and thus the greatest amount of reduced Ag-nanoparticles, as compared to Examples A2 and A3, which had a smaller amount of $Ag^+$ ions. The same is illustrated in FIG. 2, where Example B1 exhibited a larger peak as compared to Examples B2 and B3, which had a smaller amount of $Ag^+$ ions.

TABLE 1

Silver Ion Exchange and Plasma Conditions.

| Example | Bath Composition | Plasma Exposure Conditions |
|---|---|---|
| Example A1 | 100 wt % $AgNO_3$ | $Ar/O_2$ plasma generated at 50 W for about 3 minutes |
| Example A2 | 50 wt % $AgNO_3$, 50 wt % $KNO_3$ | $Ar/O_2$ plasma generated at 50 W for about 3 minutes |
| Example A3 | 20 wt % $AgNO_3$, 80 wt % wt % $KNO_3$ | $Ar/O_2$ plasma generated at 50 W for about 3 minutes |
| Example B1 | 100 wt % $AgNO_3$ | air plasma generated at 30 W for about 3 minutes |
| Example B2 | 50 wt % $AgNO_3$, 50 wt % $KNO_3$ | air plasma generated at 30 W for about 3 minutes |
| Example B3 | 20 wt % $AgNO_3$, 80 wt % wt % $KNO_3$ | air plasma generated at 30 W for about 3 minutes |

Example 2

Examples C1-C4, D1-D4, E1-E4 and F1-F4 were prepared using the same glass composition as Examples A1-A3 and B1-B3 and were chemically strengthened in the same manner as Examples A1-A3 and B1-B3. Examples C1-C4 were then immersed in a $AgNO_3$-containing molten salt bath to ion exchange $Ag^+$ into the glass substrate, for five minutes, as shown in Table 2. The resulting articles were then exposed to air as the process gas and plasma generated at a specific power for about 3 minutes, as shown in Table 2.

TABLE 2

Silver Ion Exchange and Plasma Exposure Conditions.

| Example | Bath Composition | Plasma Conditions |
|---|---|---|
| Example C1 | 50 wt % $AgNO_3$, 50 wt % $NaNO_3$ | No exposure to plasma |
| Example C2 | | 7 W |
| Example C3 | | 10 W |
| Example C4 | | 30 W |
| Example D1 | 20 wt % $AgNO_3$, 80 wt % $NaNO_3$ | No exposure to plasma |
| Example D2 | | 7 W |
| Example D3 | | 10 W |
| Example D4 | | 30 W |
| Example E1 | 20 wt % $AgNO_3$, 80 wt % $KNO_3$ | No exposure to plasma |
| Example E2 | | 7 W |
| Example E3 | | 10 W |
| Example E4 | | 30 W |
| Example F1 | 5 wt % $AgNO_3$, 95 wt % $KNO_3$ | No exposure to plasma |
| Example F2 | | 7 W |
| Example F3 | | 10 W |
| Example F4 | | 30 W |

Figure 3:
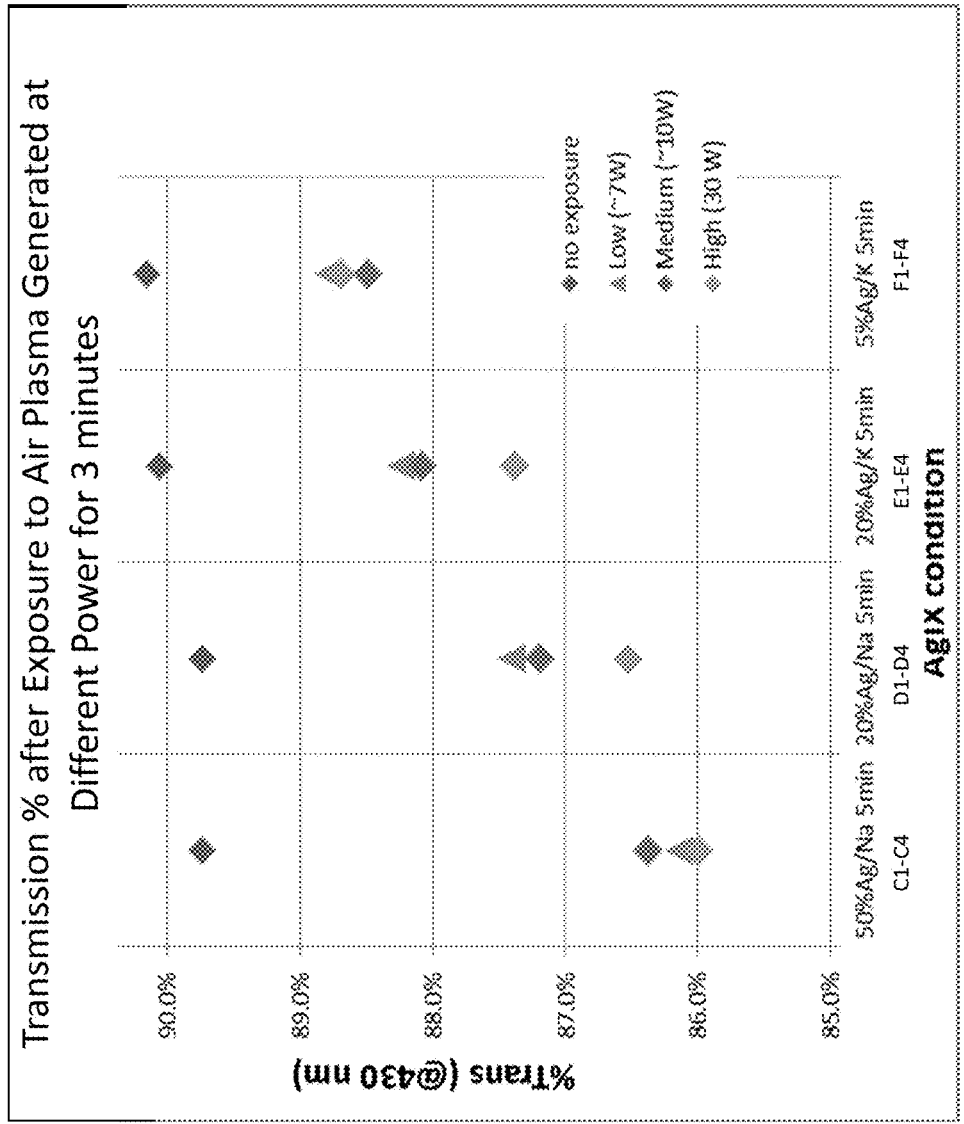
FIG. 3 is a graph illustrating the change in transmission in glass articles after exposure to certain conditions, according to one or more embodiments.

The transmission % of each of the Examples was measured at a wavelength of 430 nm. FIG. 3 includes a graph comparing the transmission of each Example. As shown in FIG. 3, no exposure to plasma or exposure to plasma generated at a lower power (e.g., 7 W) results in less of a change in transmission and thus less discoloration as compared to exposure to a plasma generated at a higher power (e.g., 30 W).

Example 3

Examples G1-G5 were prepared using the same glass composition as Examples A1-A3 and B1-B3 and were chemically strengthened in the same manner as Examples A1-A3 and B1-B3. Examples G1-G5 were then immersed in a molten salt bath that included 5 wt % $AgNO_3$ and 95 wt % $KNO_3$ to ion exchange $Ag^+$ into the glass substrate, for five minutes. The Examples were then exposed to a plasma using the process gas as air; plasma generated at two different powers for either 1 minute or 3 minutes, as shown in Table 3.

TABLE 3

Plasma Exposure Conditions.

| Example | Plasma Exposure Conditions |
|---|---|
| Example G1 | No exposure |
| Example G2 | 10 W for 1 minute |
| Example G3 | 30 W for 1 minute |
| Example G4 | 10 W for 3 minutes |
| Example G5 | 30 W for 3 minutes |

Figure 4:
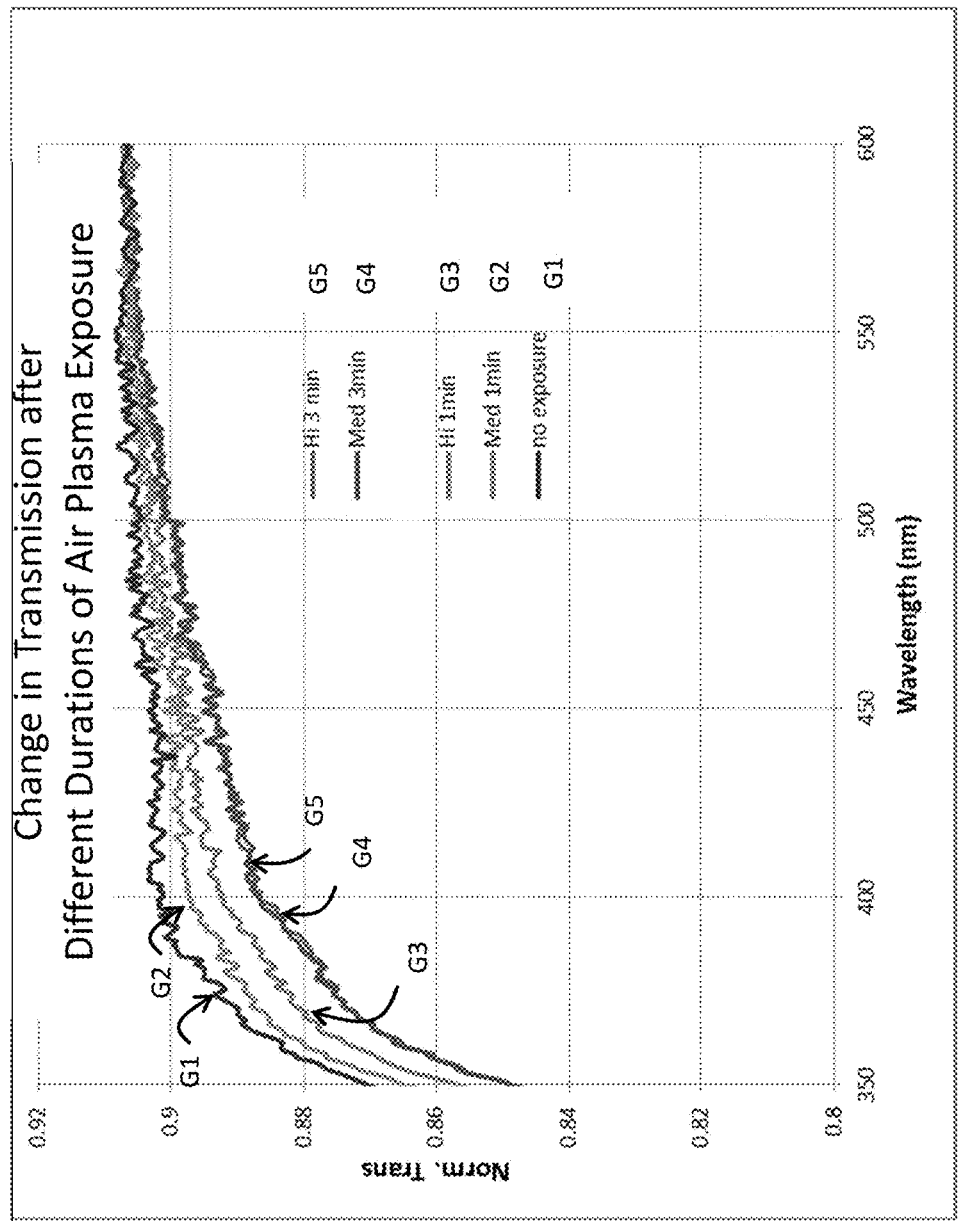
FIG. 4 is a graph illustrating the change in normalized transmission in glass articles after exposure to certain conditions, according to one or more embodiments.

The transmission % of each of the Examples was measured over a wavelength from about 350 nm to about 600 nm and normalized. Normalized transmission was obtained by taking the % trans value of G1 at 600 nm and dividing all samples 600 nm data point to obtain a normalization factor. Then all the values for the samples were divided by the corresponding factor. The normalized plot shown in FIG. 4 illustrates the relative change in the transmission % of the different Examples after exposure to plasma for different lengths of time. FIG. 4 shows that reduced exposure time to plasma generated at lower power results in the least change in transmission (or in other words, the least amount of discoloration).

Example 4

Three samples each of Examples H1-H3 (9 total samples) were prepared using three different aluminosilicate glass compositions having three different NBO amounts. Each of Examples H1-H3 were chemically strengthened in the same manner and then immersed in a $AgNO_3$—$NaNO_3$ molten bath having a specific composition, for a specific duration, as shown in Table 4. The resulting Examples H1-H3 had a $Ag_2O$ content of about 20-25 wt % as measured by the analytical technique of EMP over a region of the glass substrates from the surface of the glass substrate to a depth of about 50 nm to about 80 nm into the glass substrate. Due to the different glass compositions of Examples H1-H3, the $AgNO_3$—$NaNO_3$ molten bath composition and the length of time for which a substrate was immersed in the $AgNO_3$—$NaNO_3$ molten bath both were varied so that approximately the same amount of Ag+ ions was exchanged into all three Examples, H1-H3.

TABLE 4

NBO Content and Silver Ion Exchange Conditions

| Example | NBO Content ($Al_2O_3$-$\Sigma R_2O$) mol % | Bath Composition |
|---|---|---|
| Example H1 | −0.67 | 20 wt % $AgNO_3$, 80 wt % $NaNO_3$ 10 minutes |
| Example H2 | −6.58 | 50 wt % $AgNO_3$, 50 wt % $NaNO_3$ 20 minutes |
| Example H3 | −0.35 | 50 wt % $AgNO_3$, 50 wt % $NaNO_3$ 15 minutes |

Figure 5:
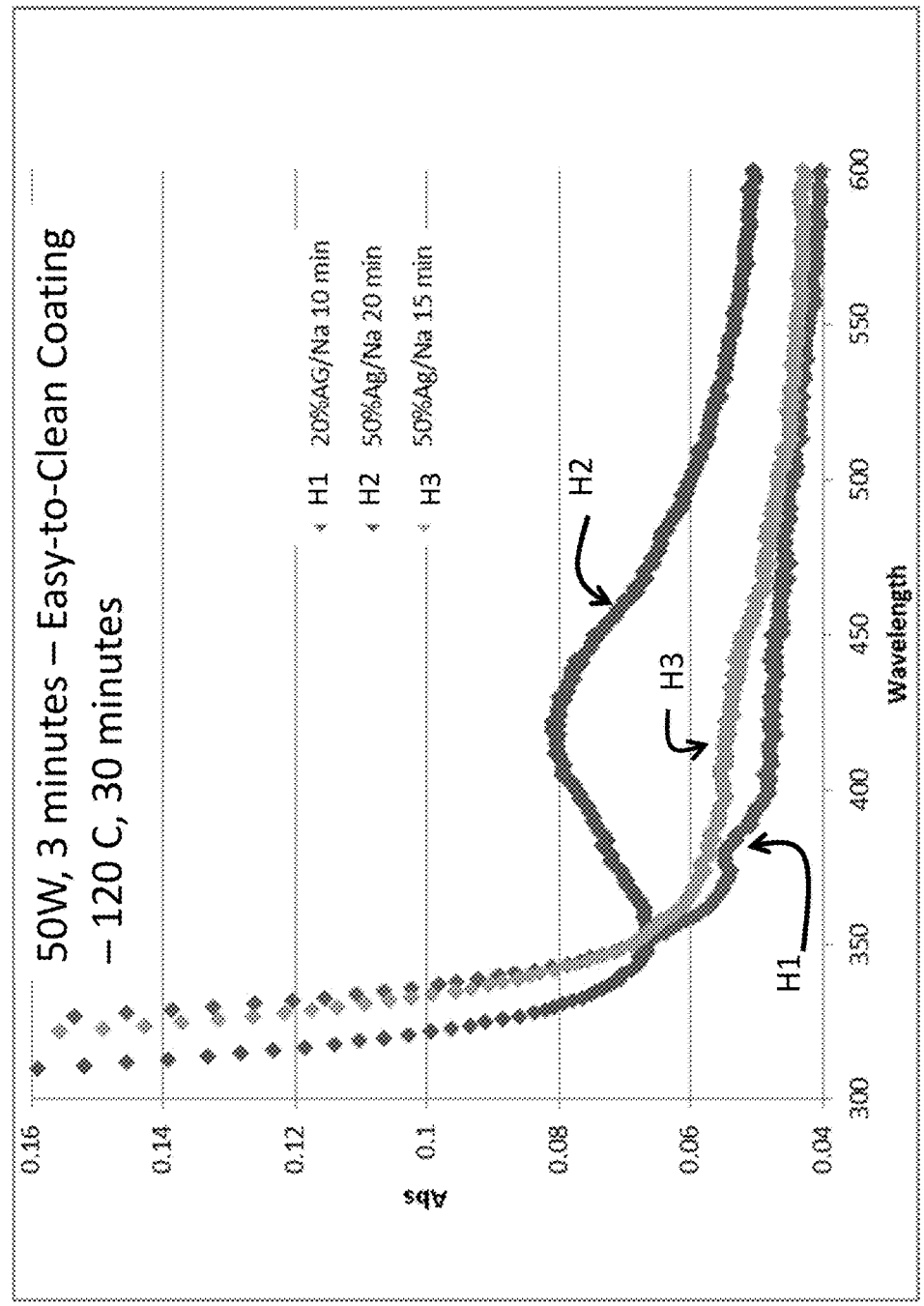
FIG. 5 is a graph illustrating the absorbence of a glass article over a wavelength range, according to one or more embodiments.
Figure 6:
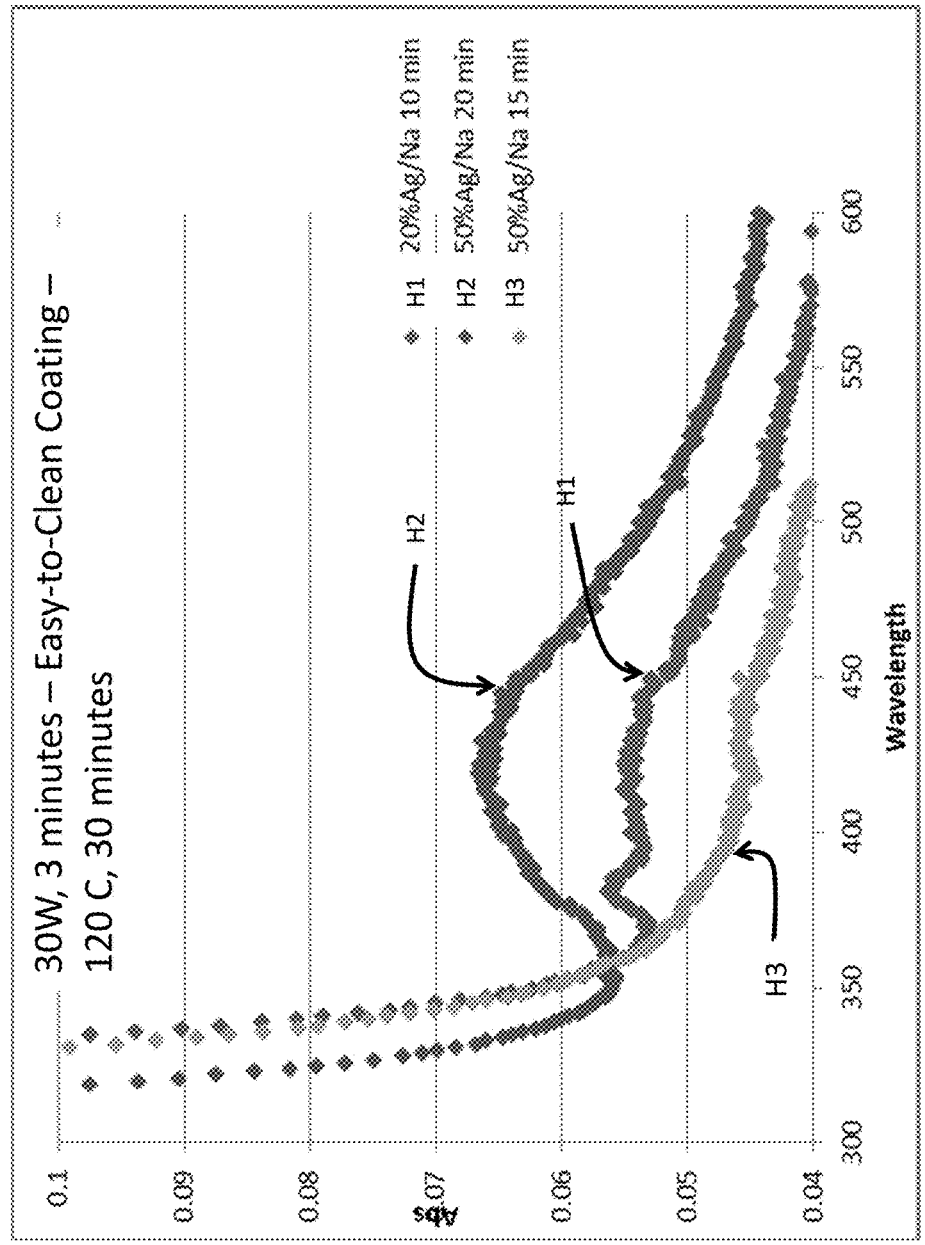
FIG. 6 is a graph illustrating the absorbance of a glass article over a wavelength range, according to one or more embodiments.
Figure 7:
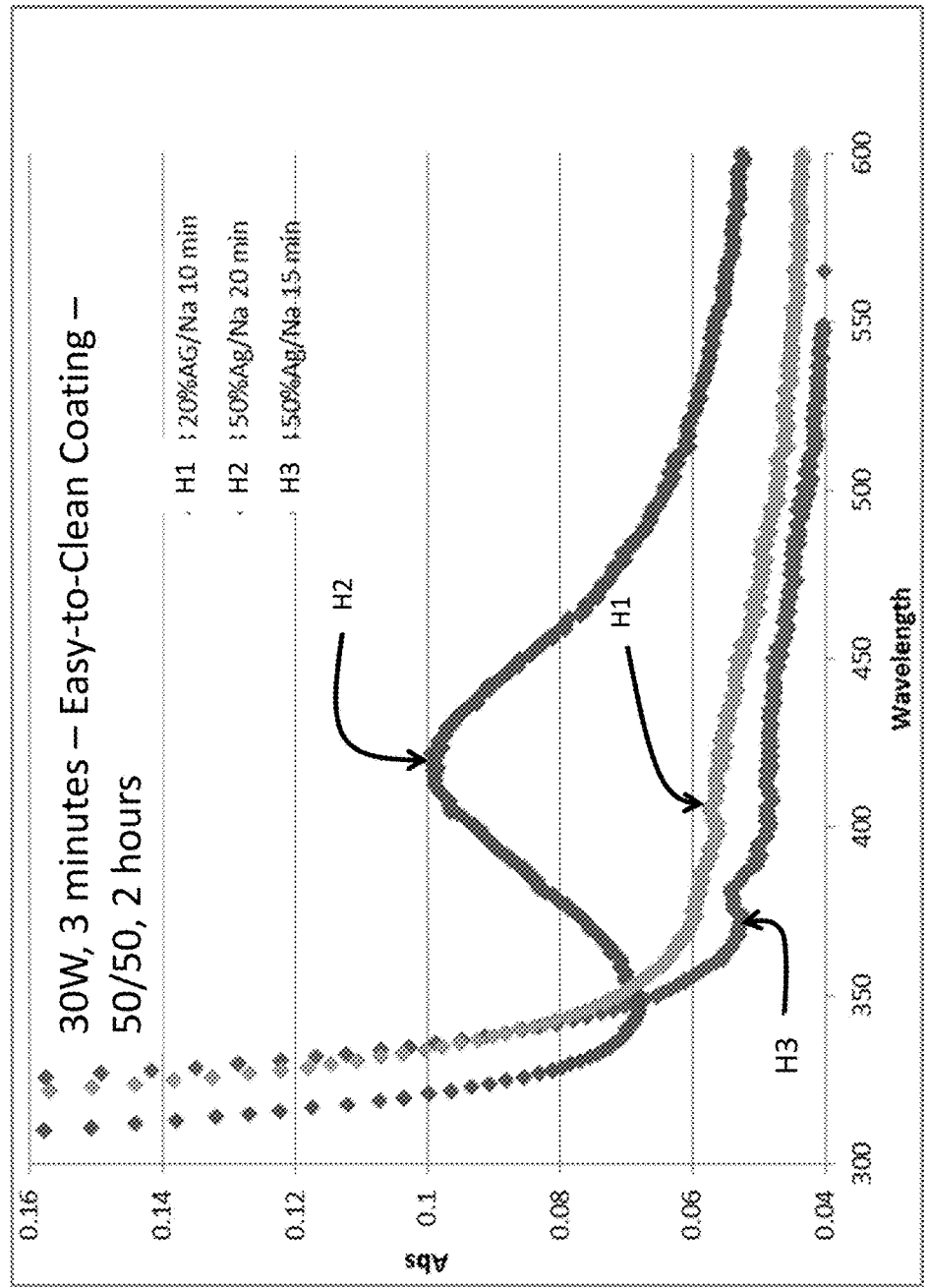
FIG. 7 is a graph illustrating the absorbance of a glass article over a wavelength range, according to one or more embodiments.

Three samples, including one according to each of Examples H1-H3, were exposed to process gas mix of Ar/$O_2$ and plasma generated at 50 W for about 3 minutes and then coated with an easy-to-clean coating and thermally cured at 120° C. for about 30 minutes. The absorbance of these three samples was measured and shown in the graph of FIG. 5. Three samples, including one according to each of Examples H1-H3, were exposed to air as the process gas and plasma was generated at 30 W for about 3 minutes and then coated with an easy-to-clean coating and thermally cured at 120° C. for about 30 minutes. The absorbance of these three samples was measured and shown in the graph of FIG. 6. The final three samples, including one according to each of Examples H1-H3, were exposed to a mix process gas Ar/$O_2$ and a plasma generated at 50 W for about 3 minutes and then coated with an easy-to-clean coating and thermally cured at 50% RH, 50° C. for about 2 hours. The absorbance of these three samples was measured and shown in the graph of FIG. 7. FIGS. 5, 6 and 7 show a surface plasmon resonance absorption in the range from about 420 nm to about 430 nm of the spectrum, indicating the reduction of $(Ag^+)_n$ to $(Ag^0)_m$ and the presence of reduced Ag-nanoparticles. As shown in FIGS. 5, 6 and 7, the sample according to Example H2, which had the highest amount of NBOs, exhibited the largest peak from about 420 nm to about 430 nm of the spectrum, indicating the most reduction of Ag+ to Ag-nanoparticles and thus the most discoloration, as compared to the samples of Examples H1 and H2, which exhibited low NBOs.

Example 5

Figure 8:
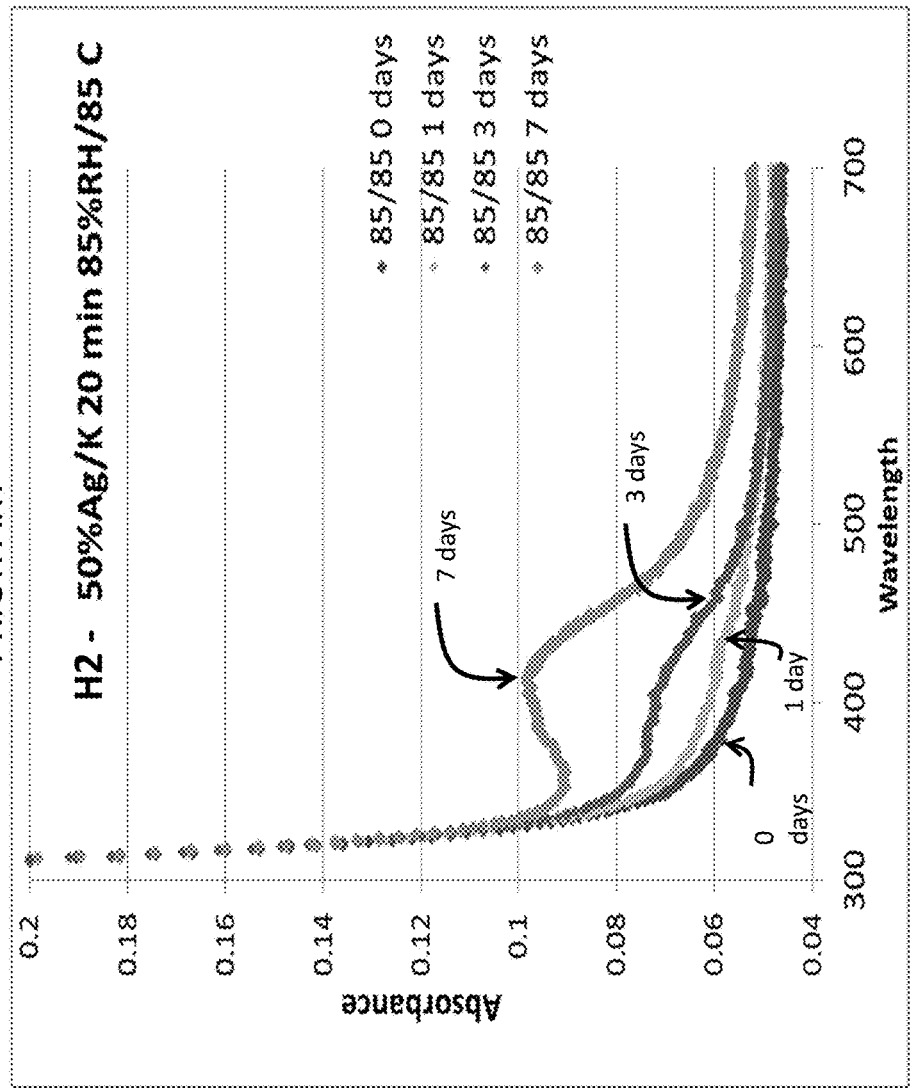
FIG. 8 is a graph illustrating the absorbance of glass articles over a wavelength range, according to the prior art.
Figure 9:
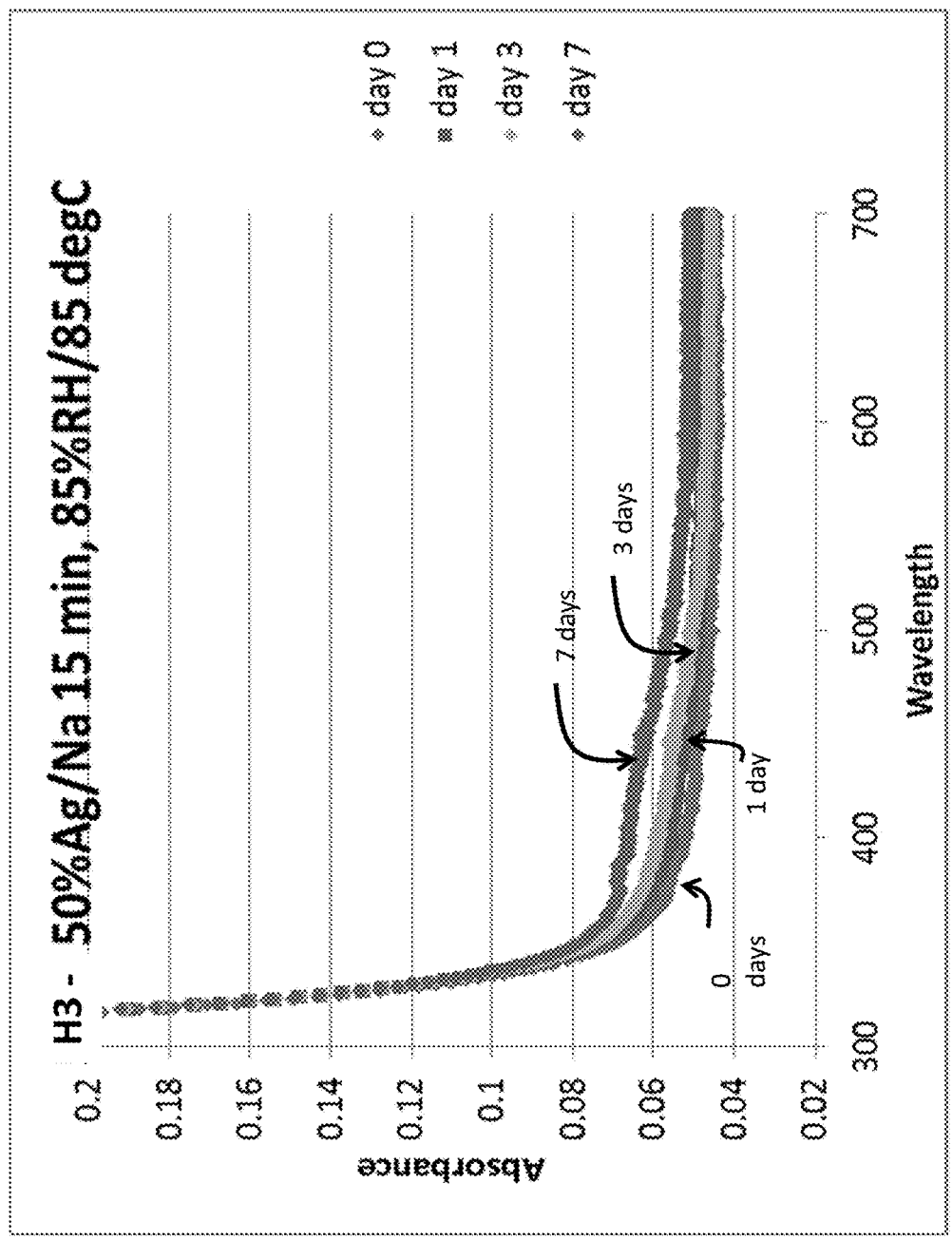
FIG. 9 is a graph illustrating the absorbance of glass articles over a wavelength range, according to one or more embodiments.

Additional samples of Examples H2 and H3 were prepared. The samples were then aged under accelerated aging conditions in air, having a relative humidity of 85% and a temperature of about 85° C. for 7 days. The absorbance of the samples was measured after one day of exposure at 85% RH and 85° C., 3 days of exposure at the same conditions and 7 days of exposure at the same conditions to determine change in absorbance, or change in the amount of reduced Ag(0) after the above accelerated aging conditions. The absorbance measurements for the samples according to Example H2 are shown in FIG. 8 and the absorbance measurements for the samples according to Example H3 are shown in FIG. 9. In both FIGS. 8 and 9, plasmon resonance peak at between 420 nm and 430 nm enlarges as the sample ages; however, the sample according to H2 shows a much larger plasmon resonance peak after 7 days, as compared to the plasmon resonance peak of the sample according to H3, after the same number of days. This indicates a greater amount of reduced Ag(0) in the sample according to Example H2, as it aged.

Example 6

Additional samples (Examples I1-I5) of having the same glass composition as Example H3 were prepared and were chemically strengthened in the same manner to each other. Each of the samples was then immersed in a $AgNO_3$—$KNO_3$ molten salt bath for 5-10 minutes, to ion exchange Ag+ into the glass substrates. The $AgNO_3$—$KNO_3$ molten salt bath had a temperature of about 350° C. The resulting samples had a surface silver concentration of about 28-30 wt %, as measured by SIMS. The samples were then subjected to elevated temperatures as shown in Table 5 for 2 hours each and then tested under the Dry Test. Under the Dry Test, an inoculum was prepared as follows: inoculating nutrient agar with a portion of a stock having a plurality of bacterial organisms to form a culture, incubating the culture to form a first incubated culture, incubating a portion of the first incubated culture with nutrient agar to form a second incubated culture, incubating a portion of the second incubated culture with nutrient agar to form a third incubated culture, incubating the third incubated culture for approximately 48 hours to form an inoculated test plate with a plurality of bacterial colonies, and suspending a portion of the plurality of bacterial colonies in a buffered test solution of Minimum Essential Medium solution with 15% Fetal Bovine Serum (FBS), adjusting the test solution to a pH of approximately 7 to 8, and adding an organic soil serum at a concentration of approximately 10% to 30% by weight to the test solution. Each of the samples was innoculated with the inoculum and incubated for about 2 hours. Each sample was then washed in a neutralizing solution to form a residual test inoculum. The number of surviving bacterial colonies per volume in the residual test inoculum was then counted to calculate the percent reduction in the number of surviving bacterial colonies in the residual test inoculum (relative to a control residual inoculum).

TABLE 5

| Heating Conditions. | |
|---|---|
| Sample | Temperature |
| I1 | Not subjected to elevated temperature |
| I2 | 120° C. |
| I3 | 180° C. |
| I4 | 200° C. |
| I5 | 250° C. |

Figure 10:
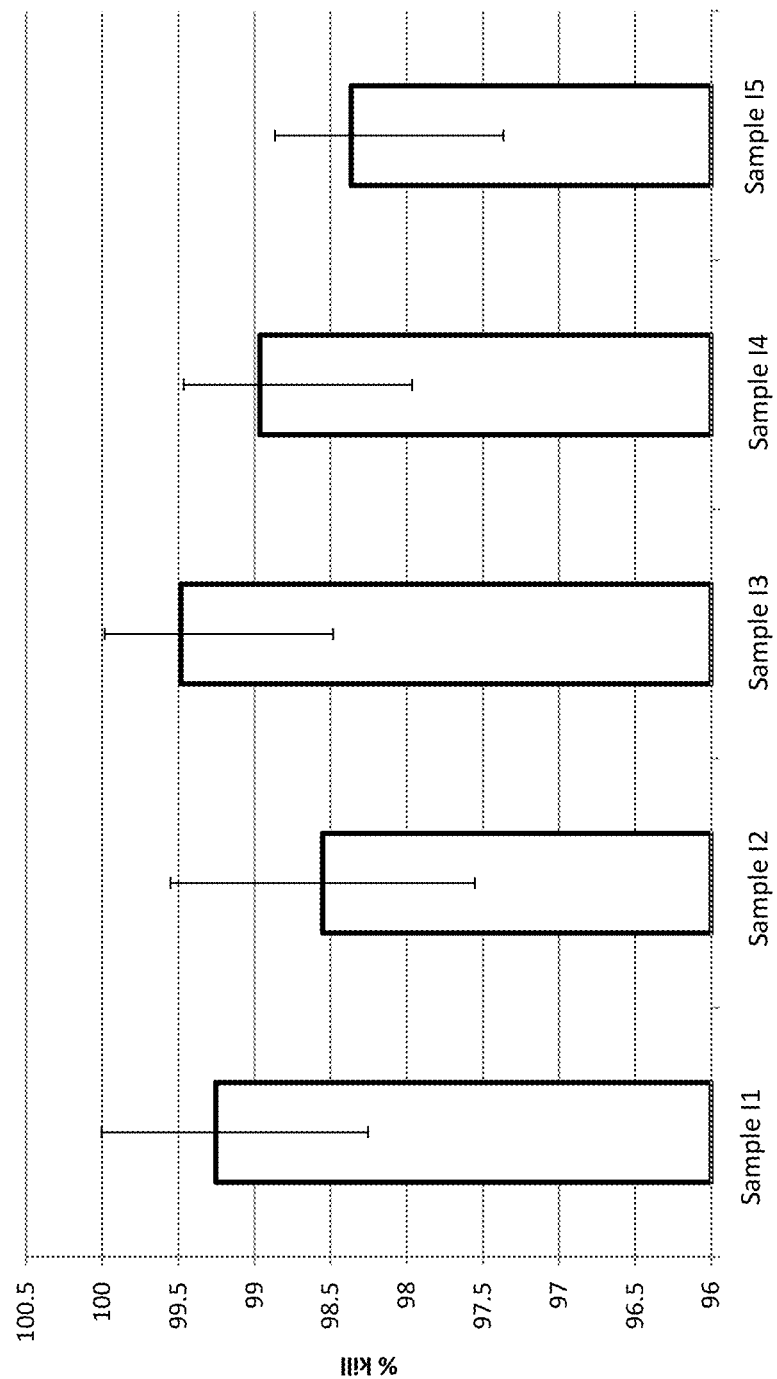
FIG. 10 is a graph illustrating the antimicrobial efficacy of one or more embodiments under a Dry Test.

FIG. 10 illustrates the reduction in bacteria (specifically, *Staphylococcus aureus, Enterobacter aerogenes, Pseudomonas aeruginosa* and *Escherichia coli*) for each sample. Samples 13 and 14 maintained about 99% kill or greater when heated to about 180° C. and about 200° C., under the Dry Test.

While the embodiments disclosed herein have been set forth for the purpose of illustration, the foregoing description should not be deemed to be a limitation on the scope of the disclosure or the appended claims. Accordingly, various modifications, adaptations, and alternatives may occur to one skilled in the art without departing from the spirit and scope of the present disclosure or the appended claims.

What is claimed is:

1. An antimicrobial glass article, comprising:
a glass substrate comprising a compressive stress layer that extends inward from a surface of the glass substrate to a first depth therein, and an antimicrobial silver-containing region that extends inward from the surface of the glass substrate to a second depth therein, wherein the glass article exhibits substantially no discoloration that is attributable to the presence of non-bridging oxygens upon exposure of the glass article to harsh conditions,
wherein the harsh conditions are a gas mix of argon and oxygen and plasma generation at 50 W for 3 minutes, followed by a thermal treatment of 120° C. for about 30 minutes, and
further wherein the glass substrate comprises a concentration of nonbridging oxygens of about 0.67 mol % to about 0.35 mol %.

2. The antimicrobial glass article of claim 1, wherein the second depth is less than the first depth.

3. The antimicrobial glass article of claim 1, wherein the antimicrobial silver-containing region comprises a silver concentration of about 5 weight percent or greater, based on a total weight of the antimicrobial silver-containing region.

4. The antimicrobial glass article of claim 1, further comprising an additional layer disposed on the surface of the glass substrate.

5. The antimicrobial glass article of claim 4, wherein the additional layer is selected from the group consisting of a reflection-resistant coating, a glare-resistant coating, fingerprint-resistant coating, smudge-resistant coating, a color-providing composition, an environmental barrier coating, and an electrically conductive coating.

6. The antimicrobial glass article of claim 1, wherein a compressive stress of the compressive stress layer is about 200 megapascals to about 1.2 gigapascals and the depth of the compressive stress layer is less than about 100 micrometers ($\mu$m).

7. The antimicrobial glass article of claim 1, wherein the antimicrobial silver-containing region has an average thickness of less than or equal to about 20 micrometers ($\mu$m).

8. The antimicrobial glass article of claim 7, wherein a silver concentration at an outermost 50 nanometers (nm) of the antimicrobial silver-containing region is up to about 45 weight percent, based on a total weight of this outermost 50 nanometers (nm) of the antimicrobial silver-containing region.

9. The antimicrobial glass article of claim 1, wherein the antimicrobial silver-containing region has an average thickness of up to about 150 micrometers ($\mu$m).

10. The antimicrobial glass article of claim 1, wherein the antimicrobial silver-containing region has an average thickness in the range from about 20 micrometers ($\mu$m) to about 150 micrometers ($\mu$m).

11. The antimicrobial glass article of claim 9, wherein a silver concentration at an outermost 50 nanometers of the antimicrobial silver-containing region is up to about 6 weight percent, based on a total weight of this outermost 50 nanometers of the antimicrobial silver-containing region.

12. The antimicrobial glass article of claim 1, wherein the substantially no discoloration that is attributable to the presence of non-bridging oxygens upon exposure of the glass article to the harsh conditions comprises at least one of:
a change in optical transmittance of the glass article of less than or equal to about 3 percent relative to an optical transmittance before exposure to the harsh conditions,
a change in haze of the glass article of less than or equal to about 5 percent relative to a haze before exposure to the harsh conditions, and
a change in CIE 1976 color coordinates L*, a*, and b* of the glass article of less than or equal to about ±0.2, ±0.1, and ±0.1, respectively.

13. The antimicrobial glass article of claim 1, wherein the antimicrobial glass article exhibits at least a 5 log reduction in a concentration of at least *Staphylococcus aureus, Enterobacter aerogenes,* and *Pseudomonas aeruginosa* bacteria under JIS Z 2801 (2000) testing conditions.

14. The antimicrobial glass article of claim 1, wherein the antimicrobial glass article exhibits at least a 3 log reduction in a concentration of at least *Staphylococcus aureus, Enterobacter aerogenes,* and *Pseudomonas aeruginosa* bacteria under modified JIS Z 2801 (2000) testing conditions, wherein the modified conditions comprise heating the antimicrobial glass article to a temperature of about 23 degrees Celsius to about 37 degrees Celsius at a humidity of about 38 percent to about 42 percent for about 24 hours followed by drying for about 6 hours to about 24 hours.

15. The antimicrobial glass article of claim 1, wherein the antimicrobial glass article exhibits at least a 2 log reduction in the concentration of at least *Staphylococcus aureus*, *Enterobacter aerogenes*, and *Pseudomonas aeruginosa* bacteria under a Dry Test.

16. The antimicrobial glass article of claim 1, wherein the antimicrobial glass article is selected from the group consisting of a portion of a touch-sensitive display screen or cover plate for an electronic device, a non-touch-sensitive component of an electronic device, a surface of a household appliance, a surface of medical equipment, a biological or medical packaging vessel, and a surface of a vehicle component.

17. A method of making an antimicrobial glass article, the method comprising: providing a glass substrate;
forming a compressive stress layer that extends inward from a surface of the glass substrate to a first depth; and
forming an antimicrobial silver-containing region that extends inward from the surface of the glass substrate to a second depth, wherein the glass article undergoes substantially no discoloration that is attributable to the presence of non-bridging oxygens upon exposure of the glass article to harsh conditions,
wherein the harsh conditions are a gas mix of argon and oxygen and plasma generation at 50 W for 3 minutes, followed by a thermal treatment of 120° C. for about 30 minutes, and
further wherein the glass substrate comprises a concentration of nonbridging oxygens of about 0.67 mol % to about 0.35 mol %.

18. The method of claim 17, wherein the second depth is less than the first depth.

19. The method of claim 17, wherein the antimicrobial silver-containing region comprises a silver concentration of about 5 weight percent or greater, based on the total weight of the antimicrobial silver-containing region.

20. The method of claim 17, further comprising forming an additional layer on at least a portion of the surface of the substrate, wherein the additional layer is selected from the group consisting of a reflection-resistant coating, a glare-resistant coating, fingerprint-resistant coating, smudge-resistant coating, a color-providing composition, an environmental barrier coating, and an electrically conductive coating.

21. The method of claim 17, wherein a compressive stress of the compressive stress layer is about 200 megapascals to about 1.2 gigapascals and the depth of the compressive stress layer is less than about 100 micrometers (μm), and the antimicrobial silver-containing region has an average thickness of less than or equal to about 20 micrometers (/lm).

22. The method of claim 21, wherein a silver concentration at an outermost 50 nanometers of the antimicrobial silver-containing region is up to about 45 weight percent, based on a total weight of this outermost 50 nanometers of the antimicrobial silver-containing region.

23. The method of claim 17, wherein a compressive stress of the compressive stress layer is about 200 megapascals to about 1.2 gigapascals and the depth of the compressive stress layer is less than about 100 micrometers (μm), and the antimicrobial silver-containing region has an average thickness of up to about 150 micrometers (μm).

24. The method of claim 17, wherein the antimicrobial silver-containing region has an average thickness in the range from about 20 micrometers (μm) to about 150 micrometers (μm).

25. The method of claim 23, wherein a silver concentration at an outermost 50 nanometers of the antimicrobial silver-containing region is up to about 6 weight percent, based on a total weight of this outermost 50 nanometers of the antimicrobial silver-containing region.

26. The method of claim 17, wherein the substantially no discoloration that is attributable to the presence of non-bridging oxygens upon exposure of the glass article to the harsh conditions comprises at least one of:
a change in optical transmittance of the glass article of less than or equal to about 3 percent relative to an optical transmittance before exposure to the harsh conditions,
a change in haze of the glass article of less than or equal to about 5 percent relative to a haze before exposure to the harsh conditions, and
a change in CIE 1976 color coordinates L*, a*, and b* of the glass article of less than or equal to about ±0.2, ±0.1, and ±0.1, respectively.

27. The method of claim 17, wherein forming the compressive stress layer and forming the antimicrobial silver-containing region occur simultaneously.

* * * * *

UNITED STATES PATENT AND TRADEMARK OFFICE
CERTIFICATE OF CORRECTION

PATENT NO. : 9,567,259 B2  
APPLICATION NO. : 14/176470  
DATED : February 14, 2017  
INVENTOR(S) : Jaymin Amin et al.

It is certified that error appears in the above-identified patent and that said Letters Patent is hereby corrected as shown below:

In the Claims

| No. | Column | Line | Description |
|---|---|---|---|
| 1 | 19 | 60-61 | The phrase "about 0.67 mol% to about 0.35 mol %" should appear as follows:<br>--about -0.67 mol % to about -0.35 mol %--. |
| 2 | 21 | 27-28 | The phrase "about 0.67 mol% to about 0.35 mol %" should appear as follows:<br>--about -0.67 mol % to about -0.35 mol %--. |

Signed and Sealed this  
Nineteenth Day of June, 2018

Andrei Iancu  
*Director of the United States Patent and Trademark Office*